(12) United States Patent
Chau et al.

(10) Patent No.: US 9,877,831 B2
(45) Date of Patent: Jan. 30, 2018

(54) CONFORMAL EXPANSION OF PROSTHETIC DEVICES TO ANATOMICAL SHAPES

(71) Applicant: Edwards Lifesciences Corporation, Irvine, CA (US)

(72) Inventors: Mark Chau, Aliso Viejo, CA (US); Travis Zenyo Oba, Yorba Linda, CA (US); Tammy Huntley, Santa Ana, CA (US); Qinggang Zeng, Aliso Viejo, CA (US); August R. Yambao, Temecula, CA (US); Rafael Pintor, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 15 days.

(21) Appl. No.: 15/097,146

(22) Filed: Apr. 12, 2016

(65) Prior Publication Data
US 2016/0220368 A1 Aug. 4, 2016

Related U.S. Application Data

(63) Continuation of application No. 14/089,723, filed on Nov. 25, 2013, now Pat. No. 9,314,334, which is a continuation of application No. 12/618,023, filed on Nov. 13, 2009, now Pat. No. 8,591,567.

(60) Provisional application No. 61/117,902, filed on Nov. 25, 2008.

(51) Int. Cl.
*A61F 2/06* (2013.01)
*A61F 2/24* (2006.01)

(52) U.S. Cl.
CPC ............ *A61F 2/2433* (2013.01); *A61F 2/243* (2013.01); *A61F 2/2418* (2013.01); *A61F 2220/0008* (2013.01); *A61F 2230/0054* (2013.01); *A61F 2250/0003* (2013.01)

(58) Field of Classification Search
CPC ...... A61F 2/2433; A61F 2/2418; A61F 2/243; A61F 2250/0003; A61F 2230/0054; A61F 2220/0008; A61F 2/2427
See application file for complete search history.

(56) References Cited

U.S. PATENT DOCUMENTS

| | | | | |
|---|---|---|---|---|
| 5,658,311 A * | 8/1997 | Baden | ...................... | A61F 2/958 604/164.03 |
| 6,039,749 A * | 3/2000 | Marin | ....................... | A61F 2/07 604/103.07 |
| 6,245,040 B1 * | 6/2001 | Inderbitzen | ......... | A61M 25/104 604/103.07 |
| 2003/0187493 A1 * | 10/2003 | Campbell | ............. | A61F 2/0095 623/1.11 |
| 2004/0210304 A1 * | 10/2004 | Seguin | .................. | A61F 2/2409 623/2.11 |

(Continued)

*Primary Examiner* — Richard Louis
(74) *Attorney, Agent, or Firm* — Guy Cumberbatch; Pui Tong Ho

(57) ABSTRACT

A system for expanding a device in a conduit or orifice of a human body includes a balloon member that is movable from a first configuration to a second configuration. External surfaces of the balloon member can collectively have a non-cylindrical cross-section relative to a main axis of the balloon member, such that the external surfaces of the balloon member generally conform to the anatomical shape of the conduit or orifice when the balloon member is in the second configuration.

24 Claims, 17 Drawing Sheets

(56) References Cited

U.S. PATENT DOCUMENTS

2005/0234546 A1* 10/2005 Nugent ................ A61F 2/2412
623/2.11
2008/0114294 A1* 5/2008 Holman ............ A61M 25/1038
604/96.01

* cited by examiner

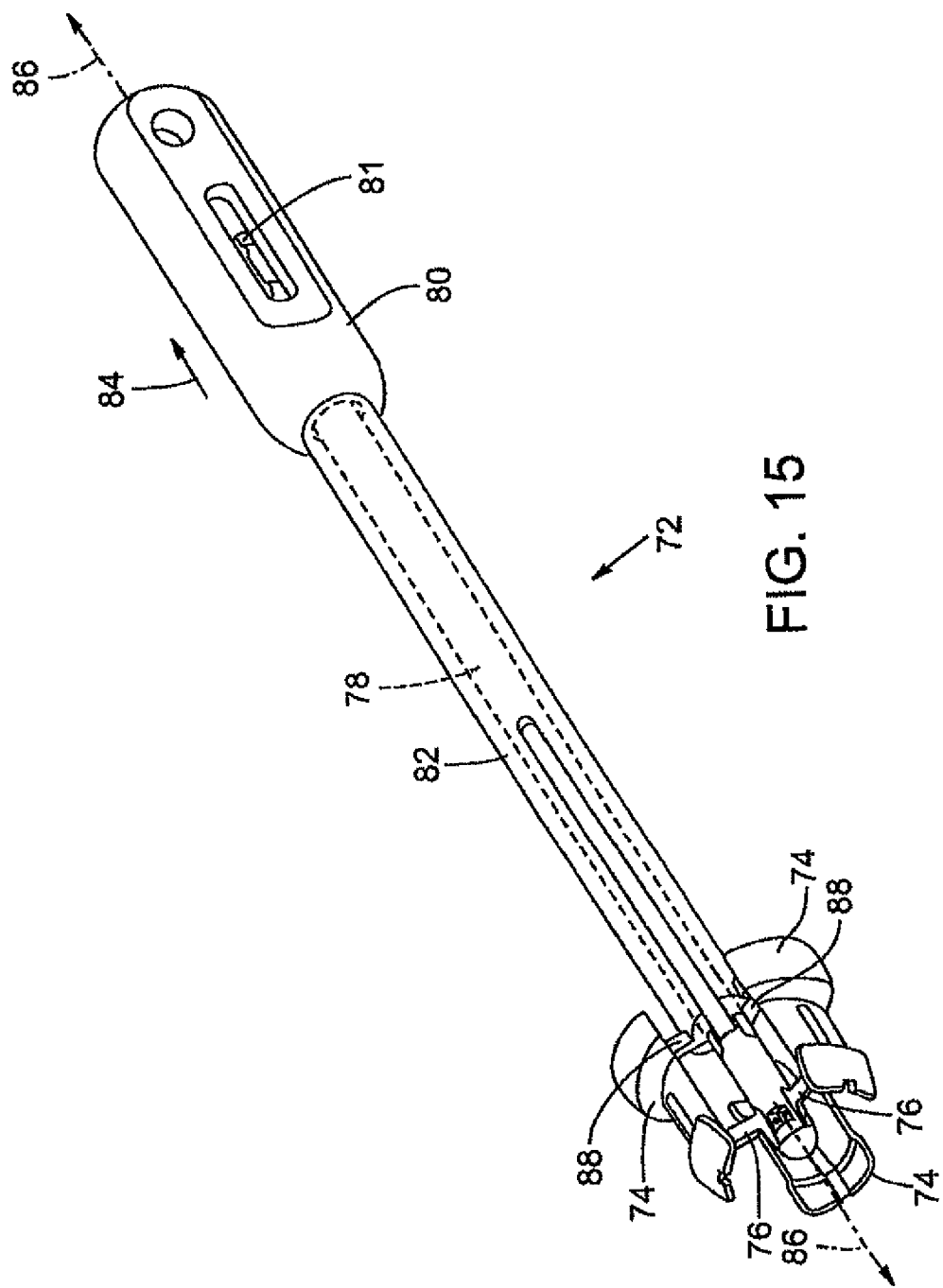

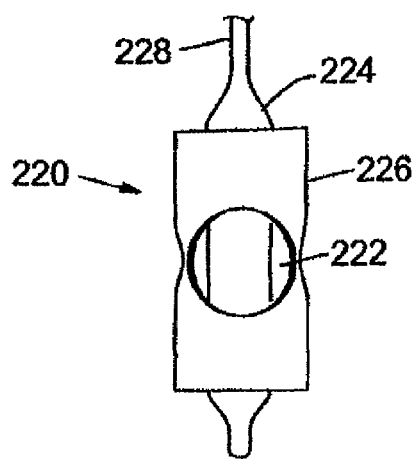
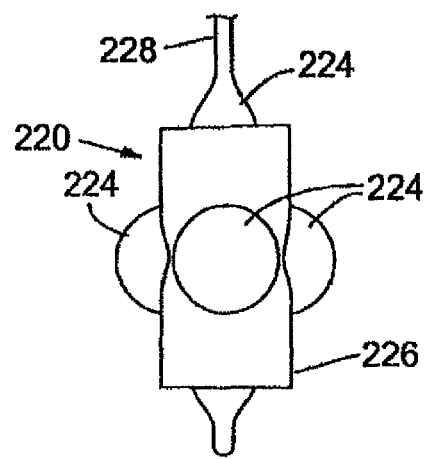
FIG. 25A  FIG. 26A
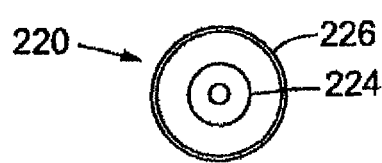
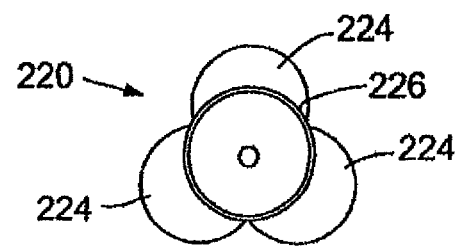
FIG. 25B  FIG. 26B

CONFORMAL EXPANSION OF PROSTHETIC DEVICES TO ANATOMICAL SHAPES

CROSS REFERENCE TO RELATED APPLICATIONS

This application is a continuation of U.S. patent application Ser. No. 14/089,723, filed Nov. 25, 2013, which is a continuation of U.S. patent application Ser. No. 12/618,023, filed Nov. 13, 2009, now U.S. Pat. No. 8,591,567, which claims the benefit of U.S. Patent Application No. 61/117,902 filed Nov. 25, 2008, the entire disclosures all of which are incorporated by reference.

FIELD OF THE INVENTION

The present invention concerns embodiments of a system for implanting a prosthetic device, such as an anatomical frame, into an orifice of a patient.

BACKGROUND OF THE DISCLOSURE

When treating certain medical conditions, it is sometimes desirable to expand a frame or other radially expandable member in an orifice or conduit of a patient's body. For example, expandable tubes called stents are commonly inserted into a natural conduit of a patient's body and expanded inside the conduit to hold the conduit in an open position. Such expandable stents can be used to expand, widen, or otherwise provide structural support to various conduits of the human body, including, for example, arteries, veins, bile ducts, the esophagus, and the colon. In other treatment procedures, prosthetic heart valves that include a frame member are implanted into the body at a treatment site (e.g., a heart valve annulus). These prosthetic heart valves can be positioned in the heart valve annulus by expanding the frame member to roughly the size of the valve annulus.

The expansion of such frames in the body can be performed using a balloon member, such as a balloon. For example, a method can involve positioning a frame on a balloon of a balloon catheter, maneuvering the balloon and frame to the treatment site, and inflating the balloon with a fluid to expand the frame to the desired size. Many orifices or conduits in the body, such as the native aortic valve annulus, have non-cylindrical shapes. Unfortunately, current balloon members and methods do not provide a convenient and effective way to expand a frame or other expandable member so that it conforms to a non-cylindrical orifice or conduit.

SUMMARY OF THE INVENTION

In one embodiment an apparatus for radially expanding a prosthetic device in a conduit or orifice of a human body is provided. The apparatus comprises a balloon member that has a main axis and an outer mounting surface for mounting the prosthetic device in a crimped state thereon. The balloon member can be configured to expand radially outwards from a first configuration to a second configuration to expand the prosthetic device to an expanded shape having a non-circular cross-sectional profile perpendicular to the main axis of the balloon member. The balloon member can be configured to expand the prosthetic device to generally conform to an anatomical shape of the conduit or orifice. The balloon member can also comprise a plurality of shape-forming members that have a plurality of external surfaces. The plurality of external surfaces can form at least a portion of the mounting surface of the balloon member. When the balloon member is in the second configuration, the external surfaces of the shape-forming members can collectively have a non-circular cross-sectional profile perpendicular to the main axis of the balloon member.

In specific implementations, the plurality of shape-forming members include three or more shape-forming members. In other specific implementations, the external surfaces of the shape-forming members can collectively generally conform to the trilobular shape of the aortic valve annulus when the balloon member is in the second configuration. In other specific implementations, the shape-forming members can be angularly spaced around the main axis.

In specific implementations, the balloon member can further comprise a balloon member that is inflatable from a non-expanded state to an expanded state. The balloon member can be configured to move the shape-forming members radially outwards from the first configuration to the second configuration.

In specific implementations, the shape-forming members can be are adhered to an external surface of the balloon member. In other specific implementations, the shape-forming members can be configured to form a substantially closed ring shape when the balloon member is in the non-expanded state.

In specific implementations, the apparatus can further comprise an elongated shaft. One or more linkages can be connected to a distal end of the elongated shaft and to the shape-forming members. In other specific implementations, the one or more linkages can be pivotably connected to the distal end of the elongated shaft to permit radial expansion of the shape-forming members. In other specific implementations, the one or more linkages can be connected to an actuator located at a proximal end portion of the elongated shaft. The actuator can be configured to radially expand the shape-forming members via the one or more linkages.

In specific implementations, the apparatus can comprise a balloon member and a balloon-restricting member. The balloon member can be configured to expand from a non-expanded state to an expanded state and the balloon-restricting member can surround at least a portion of the balloon member. The balloon-restricting member can have a plurality of openings through which portions of the balloon member extend when the balloon is in the expanded state. The plurality of openings can be configured so that when the balloon member is in the expanded state, the balloon member has an outer profile that is non-circular in cross section perpendicular to the main axis of the balloon member. In specific implementations, the balloon-restricting member can comprise a wire frame or a tube.

In another embodiment, a delivery system for delivering a prosthetic device is provided. The system comprises a prosthetic device and a balloon member. The prosthetic device comprises a frame member, and the balloon member has a main axis and an outer mounting surface for mounting the prosthetic device in a crimped state thereon. The balloon member can be configured to expand radially outwards from a first configuration to a second configuration to expand the prosthetic device to an expanded shape having a non-circular cross-sectional profile perpendicular to the main axis of the balloon member. In specific implementations, the balloon member can comprise a balloon member having a plurality of shape-forming members attached to an external surface of the balloon member.

In another embodiment a method of expanding a prosthetic device within a conduit or orifice of a human body is provided. The method comprises providing a balloon member that has a main axis and an outer mounting surface. The method also comprises mounting the prosthetic device on the outer mounting surface of the balloon member. The method also comprises expanding the balloon member from a first configuration to a second configuration to expand the prosthetic device to an expanded shape having a non-circular cross-sectional profile perpendicular to the main axis of the balloon member. In specific implementations, the balloon member further comprises a balloon member and a plurality of shape-forming members at least partially surrounding the balloon member, and the step of expanding the balloon member comprises inflating the balloon member. In other specific implementations, when the balloon member is in the second configuration, the external surfaces of the shape-forming members collectively define an envelope curve that generally conforms to the anatomical shape of the orifice or conduit.

The foregoing and other features and advantages of the invention will become more apparent from the following detailed description, which proceeds with reference to the accompanying figures.

BRIEF DESCRIPTION OF THE DRAWINGS

FIG. 15 is a perspective view of an expanding device.

FIG. 25A is a side view of an expanding device, shown in an unexpanded configuration.

FIG. 25B is a bottom view of the expanding device of FIG. 25A.

FIG. 26A is a side view of the expanding device of FIG. 25A, shown in an expanded configuration.

FIG. 26B is a bottom view of the expanding device of FIG. 25A, shown in an expanded configuration.

DESCRIPTION OF THE PREFERRED EMBODIMENTS

In treating certain medical conditions, it can be necessary or desirable to expand a frame member, a stent, or another type of expandable prosthetic device within an orifice or conduit of the body. However, such orifices and conduits are rarely completely cylindrical and, in some instances, have relatively complex geometries. The following embodiments provide methods and apparatuses for expanding a frame or other prosthetic member to conform to the anatomical geometry of the site in the body where the frame or member is being expanded.

Figure 1:
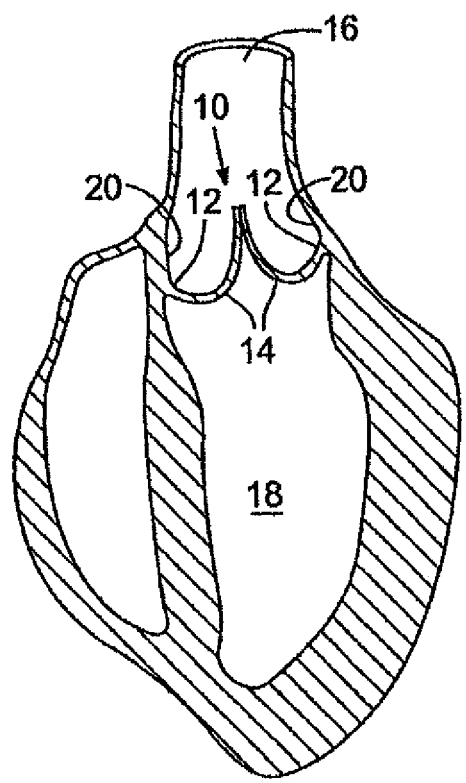
FIG. 1 is a cross-sectional view of an illustration of a portion of a heart.

FIG. 1 is a cross-sectional view of an illustration of a human heart. Aortic valve 10 includes a valve annulus 12 and, normally, three leaflets 14 (or cusps) that permit or restrict the flow of blood through aortic valve 10. Leaflets 12 (or cusps) are passive soft tissue structures attached to the aortic wall 20 at valve annulus 12 in a region called the aortic root. Aortic valve 10 is located between the aorta 16 and the left ventricle 18. As the left ventricle 18 contracts during systole, leaflets 14 are pushed aside, towards aorta wall 20 and blood flows through aortic valve 10 to aorta 16. As the left ventricle 18 relaxes during diastole, the pressure in the left ventricle 18 drops, and the leaflets 12 come together, restricting the backflow or regurgitation of blood from the aorta 16 into the left ventricle 18.

Figure 2:
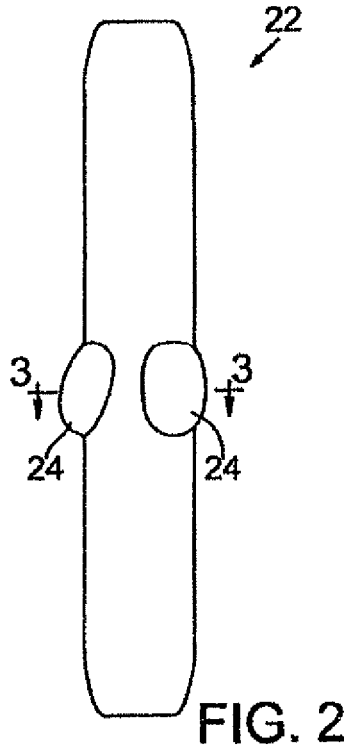
FIG. 2 is an illustration of a model of a portion of the aortic root.
Figure 3:
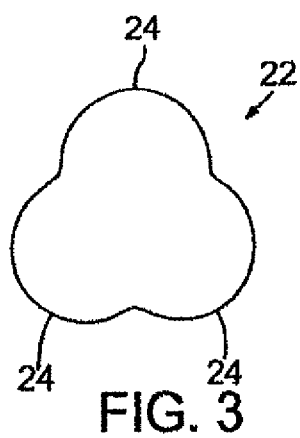
FIG. 3 is a cross section view taken along line 3-3 of FIG. 2.

FIG. 2 is a model of a portion of the aortic root 22. The three dilations (or sinuses) 24 of the aortic root 22 are a result of three corresponding recesses (or indentations) in aorta wall 20 adjacent leaflets 14. FIG. 3 is a cross-sectional view of the model of aortic root 22 shown in FIG. 2, taken at line 3-3. FIG. 3 illustrates the portion of aortic root 22 where the dilations (or sinuses) 24 have a maximum diameter. As seen in FIG. 3, the aortic root 22 (the conduit shown in this embodiment) is not cylindrical (non-circular in cross section), but rather trilobular.

It can be desirable to expand a stent, frame member, or other expandable member within the valve annulus of the aortic valve 10 (within the aortic root). Such a member can be, for example, the frame of a prosthetic valve. Alternatively, the expandable member can be a frame member deployed within the aortic annulus that forms a support structure to which a prosthetic valve (or other structure) can be expanded onto and secured. As used herein, the term "expandable member" means any prosthetic device that can be radially expanded for deployment in the body. Conventional delivery devices, such as a conventional balloon catheter, are configured to expand a prosthetic device to an expanded state having a circular cross-sectional profile along its length. Thus, a prosthetic valve or stent deployed within the aortic annulus using a conventional balloon catheter may not conform accurately to the trilobular anatomy of the aortic root.

When the expandable member comprises a first expandable frame member that is expanded in an orifice to provide a framework for securing a second expandable member (such as the stent of a prosthetic heart valve) to the first expandable member, it is desirable to expand the first expandable frame member to conform to the shape and configuration of the prosthetic heart valve that is deployed within the first frame member. For example, if the prosthetic heart valve has a trilobular shape, it is desirable to expand the first expandable member to have the same or substantially the same trilobular shape as the prosthetic heart valve. By expanding the first expandable member to the shape of the prosthetic heart valve, the frame member and prosthetic valve can be optimally sized and positioned within the valve annulus, and the occurrence of paravalvular leaks between the frame member and the native annulus as well as between the frame member and the prosthetic valve can be reduced. Moreover, because the balloon members disclosed herein can be modified and/or constructed so that they can expand an expandable member to conform to the shape of an existing prosthetic heart valve (or other prosthetic devices), the balloon members described herein can be used to expand an expandable member to provide a framework that conforms to existing, FDA-approved prosthetic surgical heart valves.

Figure 4:
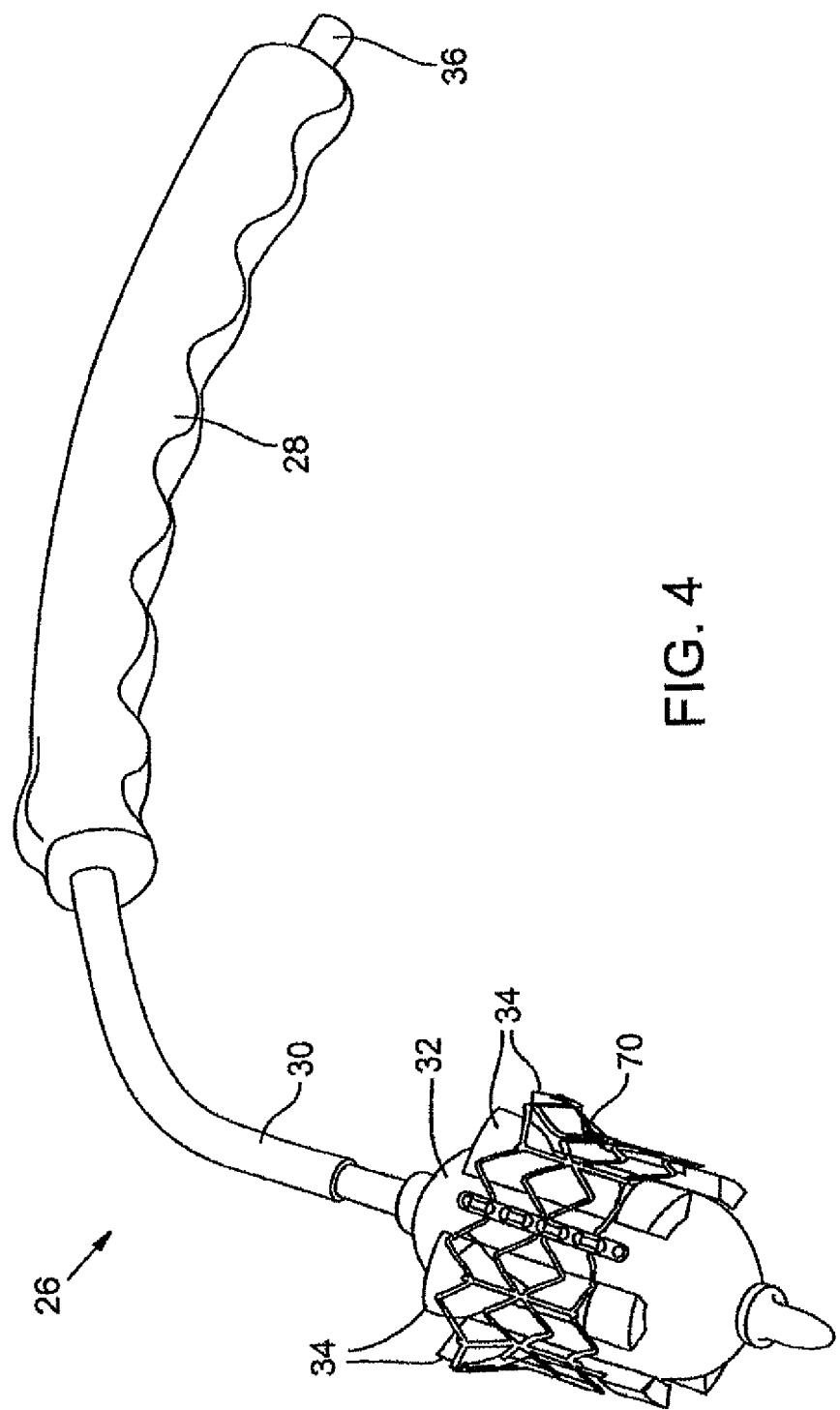
FIG. 4 is a perspective view of an expanding device with a frame member positioned on the expanding device.

FIG. 4 shows an embodiment of an apparatus for expanding an expandable member to conform to a non-circular anatomical shape of an orifice or conduit of the body. An expander 26 includes a handle 28, a shaft 30, and an expandable balloon member 32. The balloon member 32 has a plurality of longitudinally extending shape-forming members 34 (six, in this embodiment) that are spaced around the outer surface of the balloon member 32 at angularly-spaced positions and form a part of the external structure of the balloon member 32. Balloon member 32 is shown in an inflated state in FIG. 4. Desirably, shaft 30 comprises a lumen that extends from the proximal end 36 of the handle 28 to the proximal end of balloon member 32. The lumen of shaft 30 is in fluid communication with balloon member 32. An inflating device (not shown) can be connected to the proximal end 36 of the shaft 30, and a fluid that is capable of inflating the balloon member 32 can be transferred from the inflating device through the lumen to balloon member 32. Balloon inflating devices are well known and any conventional inflation means can serve to inflate balloon member 32 to expand the expandable member.

A prosthetic device (expandable member) in the form of a frame member, or stent, 70 can be positioned on the shape-forming members 34. The expansion of balloon member 32 causes shape-forming members 34 to move radially outward away from each other, which in turn expand frame member 70 to conform to the external shape of shape-forming members 34. The frame member 70 in the illustrated embodiment is adapted to be implanted within the native aortic valve and serves as a support structure for supporting a prosthetic valve deployed within frame member 70.

The shape-forming members 34 desirably have a cross-section that generally conforms to a non-cylindrical anatomical orifice or conduit in which the frame member is to be positioned and expanded. For example, the shape-forming members 34 of FIG. 4 are configured to expand the frame member to conform to the anatomy of the annulus of an aortic valve. The collective cross section of the shape-forming members 34 perpendicular to a main axis, or longitudinal, of the expandable balloon member (balloon member) is non-cylindrical. The main axis of an expander or balloon member is defined, for the purposes of this application, as the axis about which the expansion occurs. In this case, since the expansion is a result of the balloon member 32 being inflated to a larger size, the main axis is the central axis of the balloon member 32.

In the illustrated example, the shape of the shape-forming members 34 is configured so that when the balloon member 32 is expanded, the outer surfaces of the shape-forming members 34 generally conform to the shape of the aortic root 22 at that location. Since shape-forming members 34 are configured to conform to an anatomical geometry of an orifice or conduit, the expanded frame 70, which is formed by contact with shape-forming members 34 during expansion of balloon member 32, also generally conforms to the desired anatomical geometry.

It should be understood that for each embodiment discussed herein, the balloon member can be configured to expand an expandable member or prosthetic device to generally conform to the non-circular shape of an anatomical orifice or conduit. Alternatively, for each embodiment discussed herein, the balloon member can be configured to expand an expandable member to generally conform to a non-circular shape of a second prosthetic device (expandable member), which may or may not generally conform to a non-circular shape of the anatomical orifice or conduit in which the second prosthetic device is intended to be implanted.

Figure 5:
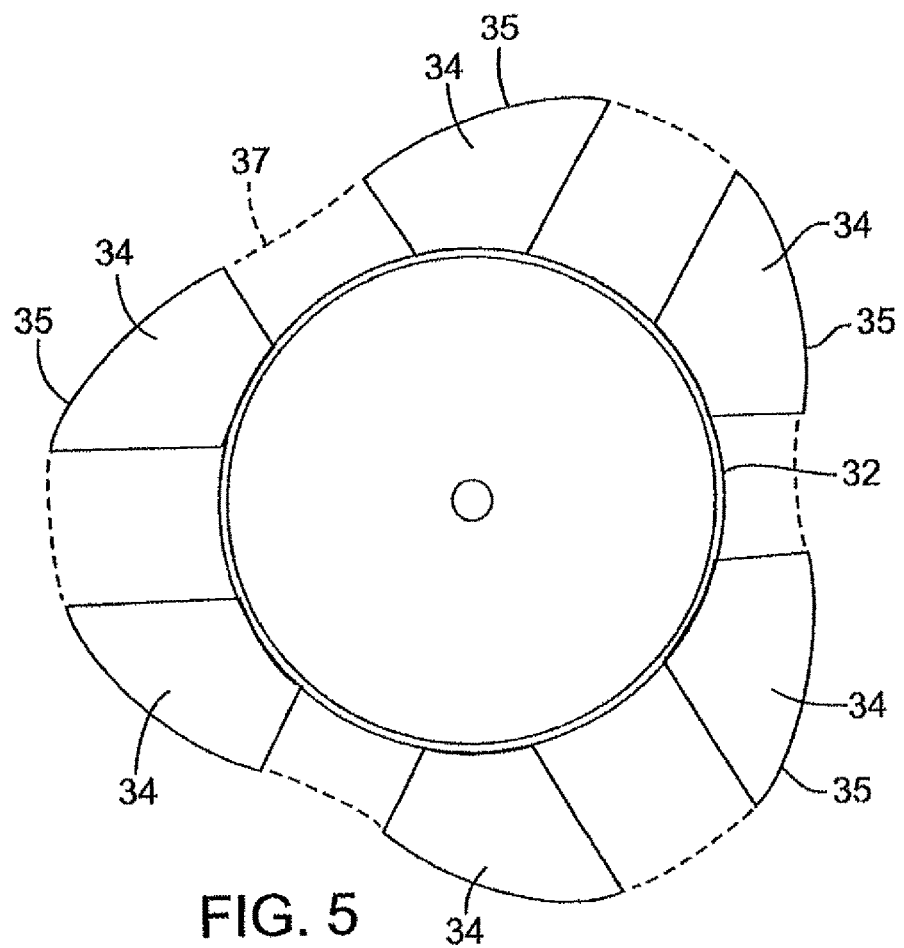
FIG. 5 is an end view of an expanding device with shape-forming members, the device being in an expanded configuration.

FIG. 5 is a top end view of the shape-forming members 34 attached to balloon member 32 in an expanded configuration. Shape-forming member 34 can have external surfaces 35 that collectively form an outer perimeter of the shape-forming members 34. Although the collective external surfaces of the shape-forming members are discontinuous, an outer envelope curve 37 is defined by the collective external surfaces 35 and the imaginary lines connecting adjacent surfaces 35 (the dashed lines in FIG. 5). When the balloon 32 is expanded, the envelope curve 37 generally conforms to the curvature of the aortic root 22 at the valve annulus, as shown in FIG. 3. The shape-forming members 34 are desirably formed of a material that is rigid enough to impart the desired shape to the frame member 70 during expansion.

Figure 6:
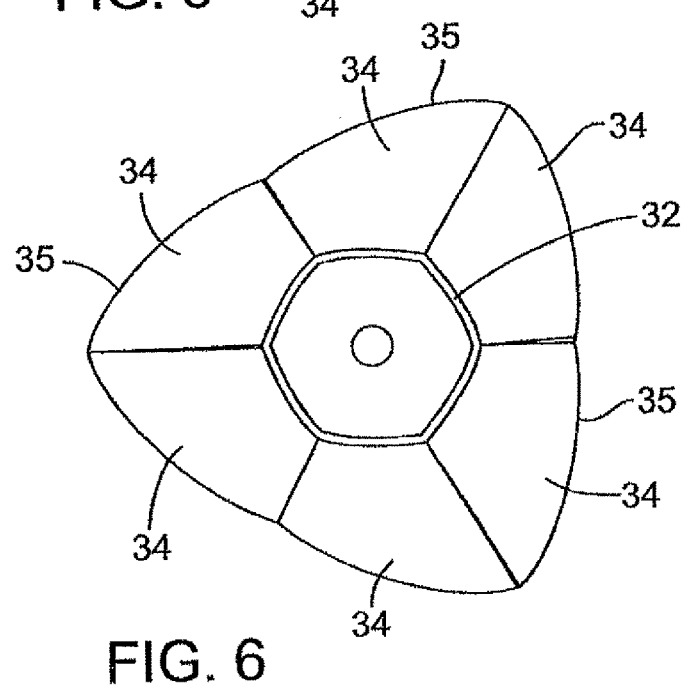
FIG. 6 is an end view of an expanding device with shape-forming members, the device being in an unexpanded configuration.

By placing the shape-forming members 34 at spaced locations around the balloon member 32, the structure can be collapsed to a smaller diameter. For example, as shown in FIG. 6, the shape-forming members 34 can collapse so that the external surfaces 35 of the shape-forming members 34 collectively form a shape that has a smaller outer perimeter. The ability of shape-forming members 34 to collapse to a smaller profile permits the distal end of expander 26 to enter and exit an orifice or conduit more easily. In addition, each shape-forming member 34 desirably is sized so that it abuts adjacent shape-forming members 34 when the shape-forming members 34 are in a collapsed (non-expanded) configuration. For example, as shown in FIG. 6, each shape-forming member 34 is configured to contact adjacent shape-forming members 34 on two sides, in order to achieve a smaller profile when in the collapsed configuration. Desirably, in the collapsed configuration, the shape-forming members form a closed-ring shape, as shown in FIG. 6. When the balloon 32 is inflated, the shape-forming members 34 move radially outward to the expanded configuration shown in FIG. 5.

Figure 7:
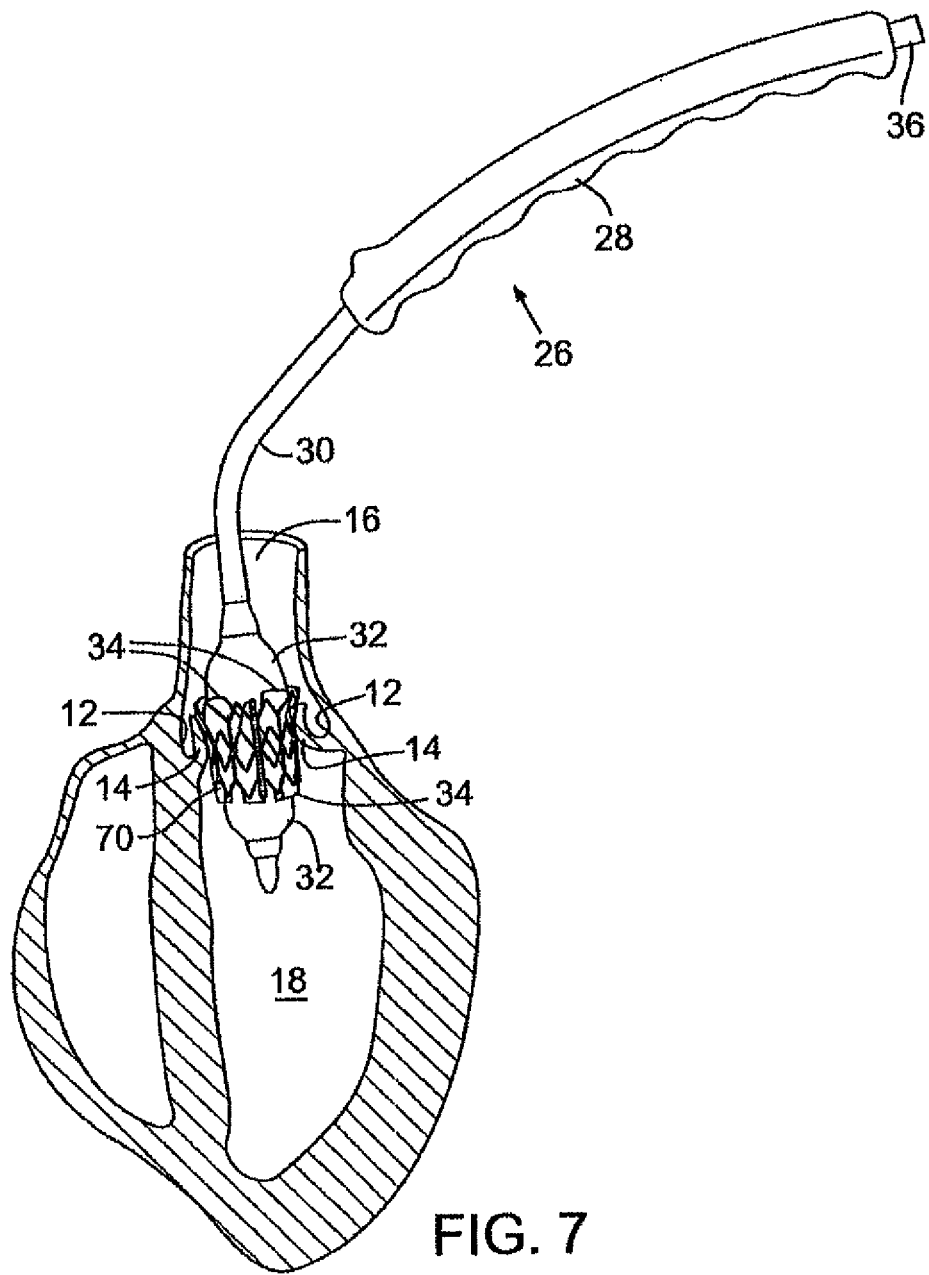
FIG. 7 is a partial cross section view of an illustration of a portion of a heart with an expanding device positioned to expand a frame member at an orifice of the heart, with the expanding device shown in an unexpanded configuration.

FIG. 7 shows an embodiment where expander 26 can be used to expand a frame member 70 to conform to the valve annulus 12 of a heart. Frame member 70 is crimped onto balloon member 32 of expander 26 when the balloon member is in the collapsed configuration (FIG. 6). Frame member 70 can be, for example, an expandable frame member (or stent) that is configured to be expanded within the orifice of the aortic valve 10, and serves as a support structure onto which a prosthetic valve can be secured. To implant the frame member 70 within the aortic valve 10, the physician can access the heart by any known surgical techniques. For example, access to the aortic valve can be achieved by an upper mini-sternotomy. Alternatively, as discussed in more detail below, the heart can be accessed percutaneously if so desired.

Figure 8:
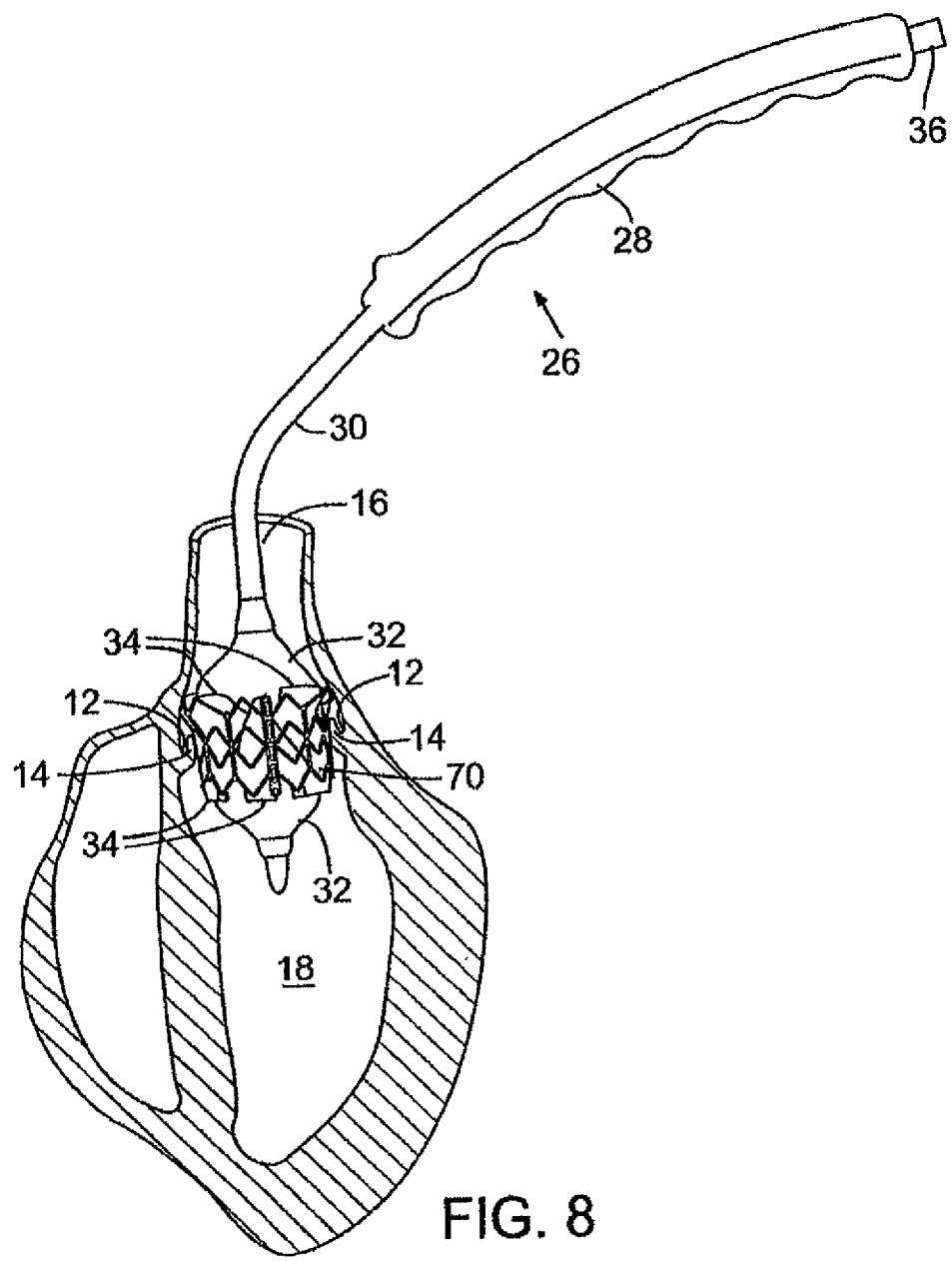
FIG. 8 is a partial cross section view of an illustration of a portion of a heart with an expanding device positioned to expand a frame member at an orifice of the heart, with the expanding device shown in an expanded configuration.

After gaining access to the aorta 16, balloon member 32 (with frame member 70 crimped on balloon member 32 and shape-forming members 34) can be inserted into the aortic valve annulus 12. Using handle 28, expander 26 can be maneuvered until frame member 70 is positioned in the desired location. Once frame member 70 is in the desired position, expander 26 can expand frame member 70 by inflation of balloon member 32, trapping valve leaflets 14 between frame member 70 and valve annulus 12 (and/or aorta wall 20), as depicted in FIG. 8. The expansion of frame member 70 can be achieved, for example, by connecting a fluid pressurizing device (or inflating device) to the fluid passageway at the distal end 36 of shaft 30 and directing fluid through the lumen of shaft 30 and into balloon member 32.

As the balloon member 32 expands under the force of the fluid from the fluid pressurizing device, the shape-forming members 34 move with the balloon and force the frame member 70 outward. As noted above, the shape-forming members 34 are desirably formed of a relatively rigid (or non-compressible) material, at least relative to the frame member (or other expandable member). As the balloon member 32 is expanded to the desired size or pressure, shape-forming members 34 move to the expanded configuration (FIG. 5) until they reach the predetermined shape of the conduit or orifice (in this case the shape of the aortic root 22). Because the shape-forming members 34 are relatively rigid (or non-compressible), as balloon member 32 expands, frame member 70 is forced outward by the shape-forming members 34 and frame member 70 is expanded to conform generally to the geometry of shape-forming members 34. After expanding frame member 70 in the valve annulus, a prosthetic heart valve can be deployed within the frame member 70, either by surgically or percutaneously accessing the heart.

In one application, for example, a prosthetic valve having a generally trilobular shaped sewing ring (typically used to suture the valve in place in conventional valve replacement surgery) can be implanted within the stent 70. Such sewing ring is positioned to seat against an inner surface of the stent, which has been expanded to have a similar trilobular cross section. In this manner, a tight seal is formed between the stent 70 and the prosthetic valve to minimize paravalvular leaks. The prosthetic valve can have a radially expanded stent connected to the support ring that is expanded against the outer stent 70 to anchor the prosthetic valve in place within the outer stent.

Figure 9:
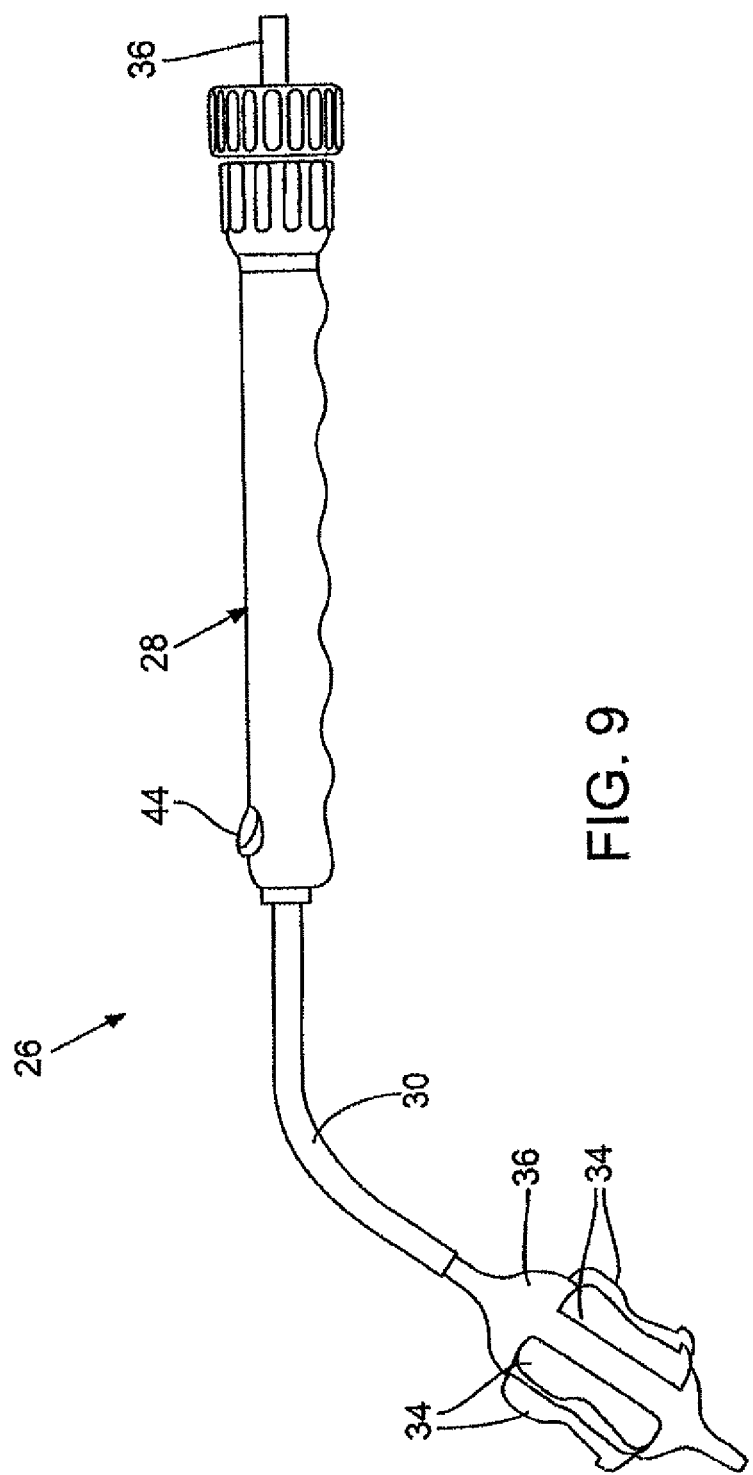
FIG. 9 is a perspective view of an expanding device.

FIG. 9 shows another embodiment of an apparatus for expanding a prosthetic device (expandable member) to conform to the anatomical shape of an orifice or conduit of the body having a non-circular cross-sectional profile. The expander 26 of FIG. 9 is similar to the expander shown in FIG. 4, except that handle 28 can be movable longitudinally relative to shaft 30. In order to fix the position of handle 28 relative to shaft 30, a position lock 44 is provided. By depressing the position lock 44, the position of the handle can be locked and unlocked relative to the shaft 30. Desirably, handle 28 is flexible and can flex with shaft 30 to permit the expander 26 to be more easily maneuvered. Also, handle 28 desirably provides a comfortable gripping surface for the physician. Except for the differences noted above and shown in FIG. 9, the expander shown in FIG. 9 functions in substantially the same manner as the expander shown in FIG. 4.

Shape-forming members, such as those discussed above, can be formed in a variety of ways. In one embodiment, the shape-forming members 34 can be formed by constructing a plurality of shape-forming members to conform to a model, such as a computer-aided design (CAD) model, of the conduit or orifice into which the frame or expandable member is to be positioned. In creating shape-forming members, a CAD model of the non-cylindrical orifice or conduit can be constructed (such as the aortic root model of FIG. 3) and the relevant portion of the CAD model can be selected and sectioned. Certain sections can be selected and retained to maintain the general outer shape of the modeled conduit or orifice, and the remaining sections can be discarded. In this manner, separate and distinct pie-shaped pieces or sections of the shape-forming members can have discontinuous (spaced-apart) external surfaces that collectively define an envelope curve that approximates the shape of the anatomical orifice or conduit when the balloon member is expanded, while permitting the shape-forming members to achieve a smaller diameter (or profile) when the balloon member is deflated.

Figure 10A:
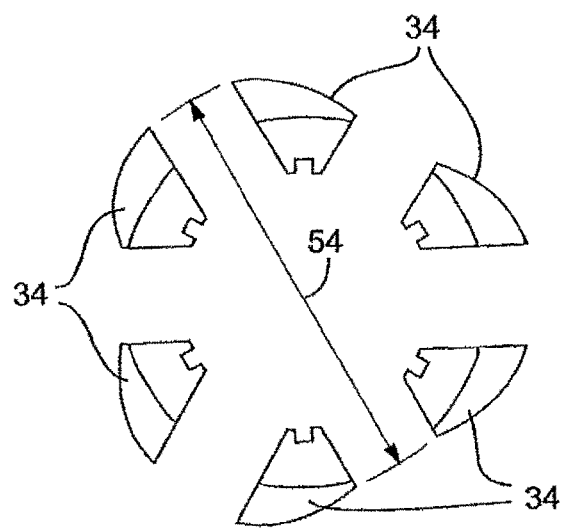
FIG. 10A is a bottom view of shape-forming members, shown in an expanded configuration without an expanding member.
Figure 10B:
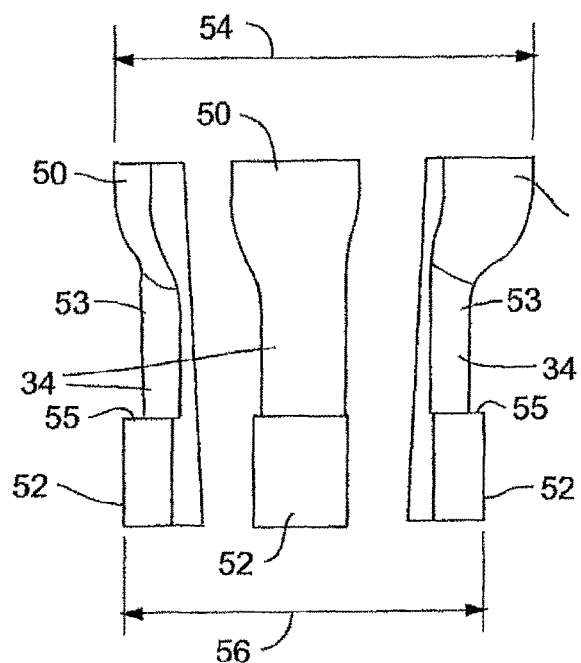
FIG. 10B is a side view of shape-forming members, shown in an expanded configuration without an expanding member.

For example, FIGS. 10A and 10B show a plurality of shape-forming members 34 in an expanded configuration (without the balloon member). The outer envelope of the expanded configuration in plan view substantially forms the shape of the conduit or orifice that is to be expanded (e.g., the valve annulus). Again, the shape-forming members have external surfaces that collectively form an outer envelope having a non-cylindrical shape perpendicular to a main axis of the balloon member. Shape-forming members 34 are desirably shaped to mate with the valve annulus, and tissue above the valve annulus in the aorta. Accordingly, in addition to having a shape that is non-cylindrical (when viewed from above, such as in FIG. 5), the shape-forming members can have a shape that varies along the length of the shape-forming members. For example, an expanded diameter 54 defined by the flared upper portions 50 of shape-forming members 34 (i.e., the portions that extend into the aorta) can be about 32 mm (or 1.260 inches), and an expanded diameter 56 defined by the lower portions 52 of shape-forming members 34 (i.e., the portion that extends into the left ventricle) can be about 23 mm (or 0.906 inches). In this manner, the expanded frame member 70 is formed with an enlarged upper portion that tapers to a smaller diameter lower portion to better conform to the aortic annulus and the aortic root immediately adjacent the annulus.

As noted above, the upper portions 50 of shape forming members 34 are preferably non-circular. In one application, upper portions 50 can be generally trilobular in cross section (perpendicular to a main axis of the balloon member) to generally conform to the shape of the aortic valve annulus. Lower portions 52 can be non-circular as well; however, it can be desirable to form lower portions 52 so that they are generally circular, as shown in FIGS. 10A and 10B. In addition, if desired, shape-forming members 34 can be formed with intermediate portions 53 that have a different diameter than upper and lower portions 50, 52. As shown in FIGS. 10-13, intermediate portions 53 can have a diameter that is smaller than the diameters of the upper portions 50 and lower portions 52. The intermediate portions 53, when expanded, can define an outer envelope that has a trilobular shape, similar to upper portions 50. In alternative embodiments, the intermediate portions 53, when expanded, can define an outer envelope that is substantially circular in cross section. To the extent that a portion of the expanded device is not circular in cross section (such as diameter of upper portions 50), the diameters discussed above are determined by taking the largest dimensions between opposing points on the outer envelope curve formed by the collective surfaces of the shape-forming members at that particular area or location.

In addition, if desirable, the transition between the lower portions 52 and the intermediate portions 53 can include lip portions 55. By configuring the shape-forming members 34 with lip portions 55, the shape-forming members can better hold a prosthetic device in place on the balloon member. For example, as shown in FIG. 4, lip portions 55 are positioned to abut an adjacent area of the prosthetic device (frame member 70), thereby restricting movement of the prosthetic device (frame member 70) in the distal direction during positioning and expansion of the balloon member.

Figure 11A:
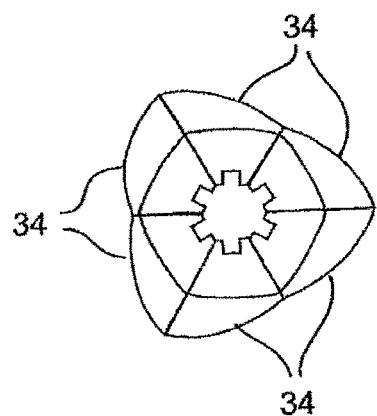
FIG. 11A is a bottom view of shape-forming members, shown in an unexpanded configuration without an expanding member.
Figure 11B:
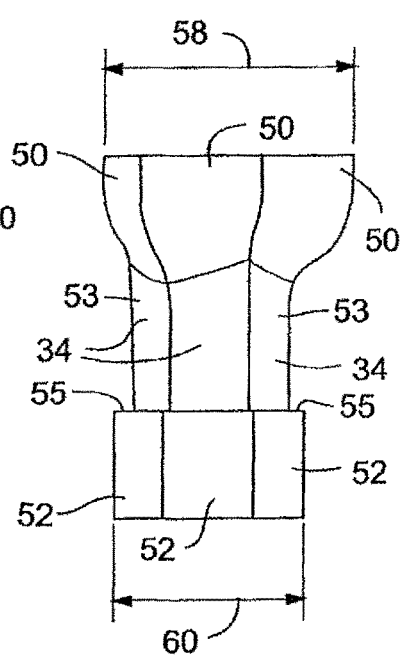
FIG. 11B is a side view of shape-forming members, shown in an unexpanded configuration without an expanding member.

Because the shape-forming members 34 have gaps or discontinuities in their expanded configuration, the shape-forming members 34 can have a smaller profile (or diameter) when the balloon member is deflated. FIGS. 11A and 11B show a plurality of shape-forming members 34 in a non-expanded (collapsed) configuration. In this configuration, a non-expanded diameter 58 defined by the upper portions 50 of shape-forming members 34 (i.e., the portions that extend into the aorta) can be about 19 mm (or 0.74803 inches), and an non-expanded diameter 60 defined by the lower portions 52 of shape-forming members 34 (i.e., the portions that extend into the left ventricle) can be about 11.25 mm (or 0.5118 inches). Accordingly, the non-expanded configuration of shape-forming members 34 can be smaller than the expanded configuration of shape-forming members 34.

Shape-forming members 34 can be configured to conform to a variety of shapes and geometries. The shape and/or geometry of shape-forming members 34 can be configured to conform to these shapes by, for example, forming a model of the conduit or orifice (such as is shown in FIGS. 2 and 3) and selecting portions of the external structure of that model to form the basis for the shape-forming members of an expanding device.

The number of shape-forming members 34 can vary. In the embodiments discussed above, there are six shape-forming members; however, there can be more or less than six members. For example, FIGS. 12A, 12B, 13A, and 13B show an embodiment with three shape-forming members 34 that has a trilobular cross-sectional profile.

Figure 12A:
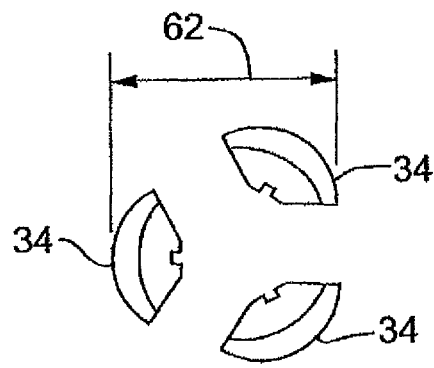
FIG. 12A is a bottom view of shape-forming members, shown in an expanded configuration without an expanding member.
Figure 13A:
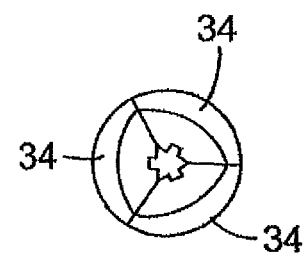
FIG. 13A is a bottom view of shape-forming members, shown in an unexpanded configuration without an expanding member.
Figure 12B:
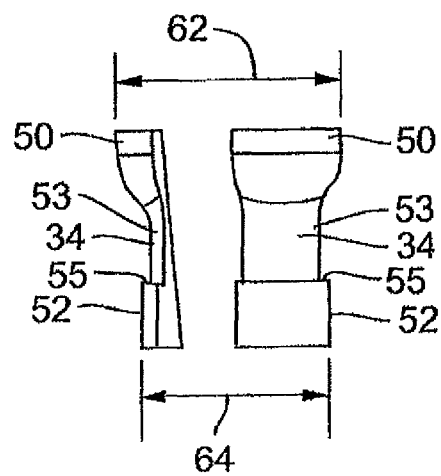
FIG. 12B is a side view of shape-forming members, shown in an expanded configuration without an expanding member.
Figure 13B:
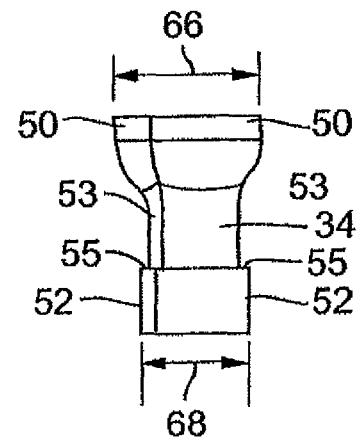
FIG. 13B is a side view of shape-forming members, shown in an unexpanded configuration without an expanding member.

The expanded and non-expanded diameters of shape-forming members shown in FIGS. 12A, 12B, 13A, and 13B can have diameters that are about the same as the diameters of the six member embodiment of FIGS. 10A, 10B, 11A, and 11B. For example, FIG. 12A shows an embodiment having a plurality of shape-forming members (three, in this embodiment) where an expanded diameter 62 defined by the upper portions 50 of shape-forming members 34 (i.e., the portions that extend into the aorta) can be about 32 mm (or 1.260 inches), and an expanded diameter 64 defined by lower portions 52 of shape-forming members 34 (i.e., the portions that extend into the left ventricle) can be about 23 mm (or 0.906 inches). FIGS. 13A and 13B show a plurality of shape-forming members 34 in a non-expanded (collapsed) configuration. In this configuration, a non-expanded diameter 66 defined by the upper portions 50 of shape-forming members 34 (i.e., the portions that extend into the aorta) can be about 19 mm (or 0.74803 inches), and a non-expanded diameter 68 defined by lower portions 52 of shape-forming members 34 (i.e., the portions that extend into the left ventricle) can be about 11.25 mm (or 0.5118 inches). It should be noted that, as discussed above, although the dimensions above are given with regard to a circular diameter, the actual shape defined by the shape-forming members is non-circular. The discussion of the inner and outer diameters is included merely for convenience in illustrating the relative expanded and non-expanded profiles of the devices.

Of course, the size of the shape-forming members can vary and the arc length of the shape-forming members can be made larger or smaller to reduce or increase, respectively, the number of shape-forming members that are used. In addition, the spaces or gaps between the shape-forming members can be increased or decreased depending on the particular requirements of the desired application.

Shape-forming members 34 can be adhered to the balloon member 32 (or other balloon member) using adhesives and/or mechanical fasteners. In lieu of or in addition to using an adhesive and/or fastener to attach the shape-forming members to the balloon, it may be desirable to apply a sleeve member that forms a layer (or overcoat) of material over at least a portion of the external surfaces of the shape-forming members and the balloon. The layer can be formed of a variety of materials, including, for example, silicone or other similar materials. If desirable, the sleeve can be formed by dip coating the balloon and shape-forming members 34 in a liquefied material, such as liquefied silicone or other similar materials. The overcoat layer can help the shape-forming members adhere to the balloon member, as well as serve as a protective material by reducing or eliminating any hard edges or points on the shape-forming members.

Figure 14A:
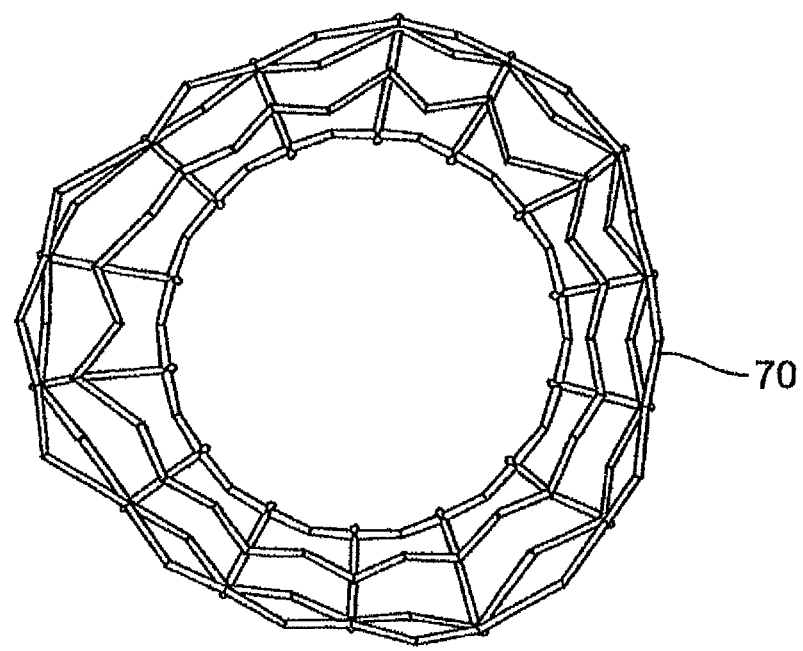
FIG. 14A is a top view of an expanded frame member.
Figure 14B:
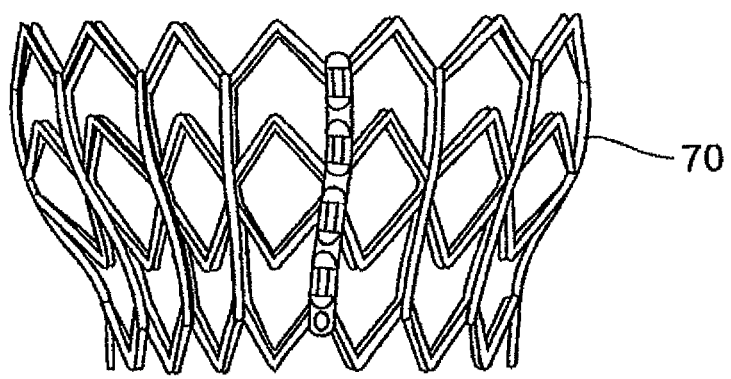
FIG. 14B is a perspective view of an expanded frame member.

As discussed above, the expandable member can be a frame member that can be expanded to fit the aortic annulus, onto which a separate prosthetic valve can be secured. As shown in FIGS. 14A and 14B and as discussed in more detail herein, frame member 70 can be expanded as shown to conform to the trilobular geometry of the aortic root 22. Frame 70 can be crimped to a smaller profile prior to expansion within the body. By crimping frame 70 to a smaller profile, it can be more easily moved through the body into position at the aortic valve annulus (or some other desired location).

FIG. 15 shows another embodiment of an apparatus for expanding an expandable member to conform to the anatomical shape of an orifice or conduit of the body. Expansion of an expandable member (e.g., frame 70 discussed above) can be achieved by means other than an inflatable balloon member. As shown in FIG. 15, expander 72 does not utilize a balloon member to cause the expansion of an expandable member. Rather, expander 72 has a plurality of shape-forming members 74 that can be forced to move radially outward or inward by applying a force along the axis 86 of the expander 72. In particular, shape-forming members 74 are attached to a plurality of linkages or arms, including distal arms 76 and proximal arms 88. Distal arms 76 are pivotably attached to an inner shaft 78. Proximal arms 88 are pivotably coupled to inner shaft 78 and to an outer shaft 82. Because proximal arms 88 are pivotably coupled to both inner shaft 78 and outer shaft 82 (but not about the same point as shown in FIG. 16A), relative movement of the two shafts is effective to pivot shape-forming members 74 radially outward, as discussed in more detail below.

Expander 72 also has a handle portion 80 connected to the outer shaft 82 at a proximal end of expander 72. Handle portion 80 can have an actuator that is configured to move shape-forming members 74 via the arms 76, 88. For example, the actuator can be a sliding mechanism 81 that is attached to inner shaft 78 at its proximal end. By moving sliding mechanism 81 axially in the proximal or distal direction, the relative positions of the outer shaft 82 and inner shaft 78 can be adjusted and the shape-forming members can be radially expanded. For example, by moving sliding mechanism 81 (and, by extension, inner shaft 78) in the proximal direction, as designated by arrow 84, proximal arms 88 are forced to pivot toward the distal end of the expander and radially inwardly from the expanded configuration shown in FIG. 15 towards an unexpanded configuration. On the other hand, by moving sliding mechanism 81 in the distal direction (the opposite direction of arrow 84), proximal arms 88 are forced toward the proximal end of the expander and radially outward to move the shape-forming members 74 radially outward to the expanded configuration shown in FIG. 15.

Arms 76 and 88 desirably are pivotably coupled to shape-forming members 74 so that the shape-forming members 74 remain substantially parallel to the main axis of the expander while moving from the unexpanded configuration to the expanded configuration and vice versa. Thus, external surfaces of shape-forming members that are substantially parallel to the main axis of the expander in the non-expanded configuration are also substantially parallel to the main axis of the expander in the expanded configuration, and at each position between the expanded and unexpanded position.

Figure 16A:
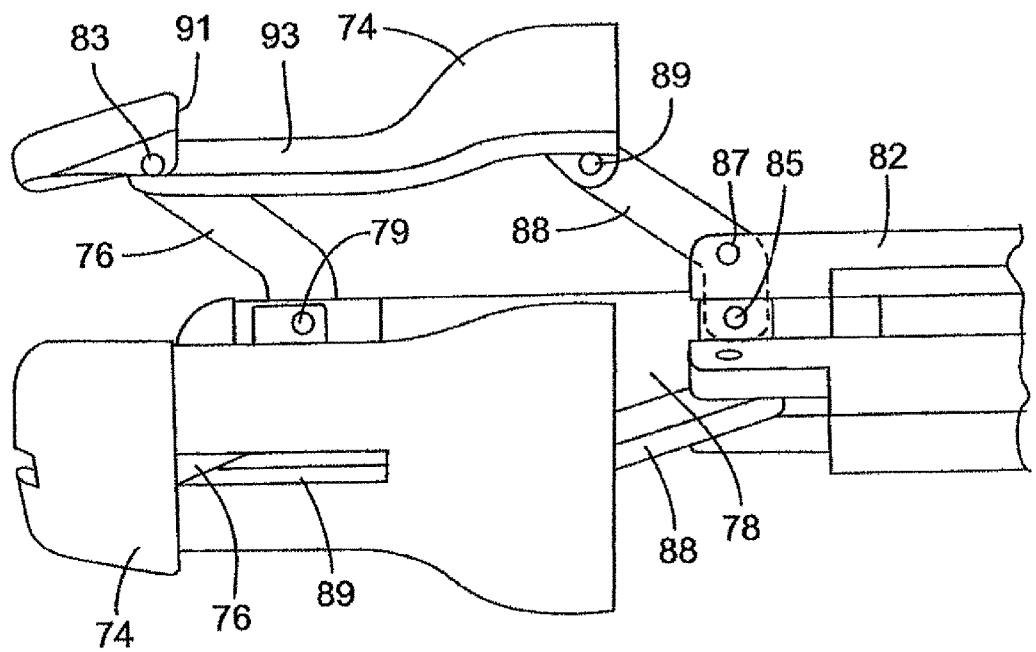
FIG. 16A is a side view of an expanding device, shown in an expanded configuration.
Figure 16B:
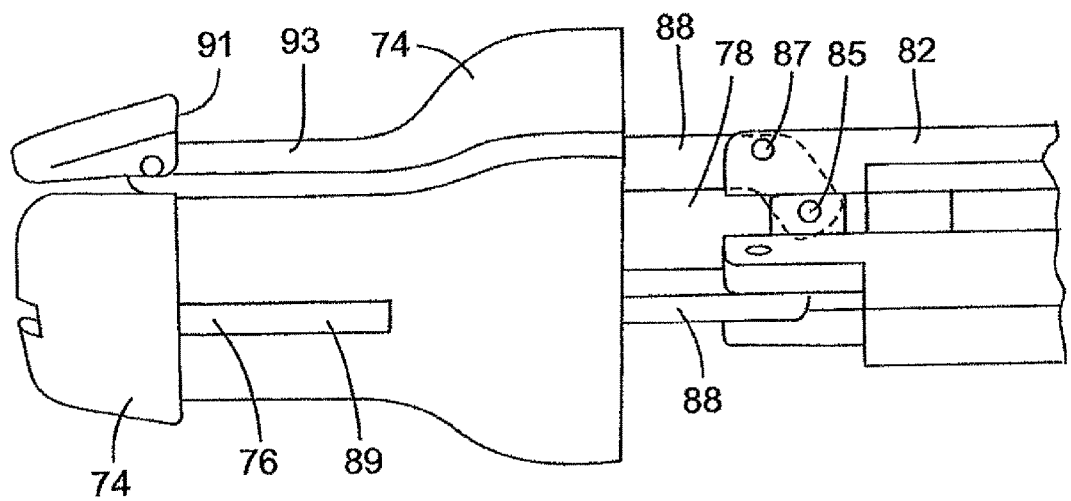
FIG. 16B is a side view of the expanding device of FIG. 16A, shown in an unexpanded configuration.

Referring now to FIGS. 16A and 16B, each shape-forming member 74 is pivotably coupled to a distal arm 76 and to a proximal arm 88. Each arm 76 is pivotably coupled at one end to inner shaft 78 at a first pivot joint 79 and at its other end to shape-forming member 74 at a second pivot joint 83. Each arm 88 is pivotably coupled to a first pivot point 85 on inner shaft 78, a second pivot point 87 on the outer shaft 82, and a third pivot point 89 on a respective shape-forming member 74. The second pivot point 87 is offset from the first pivot point 85, and is located at a point between the first pivot point 85 and the third pivot point 89. By moving sliding mechanism 81 (as shown in FIG. 15) proximally in the direction of arrow 84, the movement of inner shaft 78 relative to outer shaft 82 causes proximal arms 88 to pivot inward on inner shaft 78, moving the shape-forming members 74 to the collapsed configuration shown in FIG. 16B. Each shape-forming member 74 can also be formed with an opening (or slot) 89 to receive a portion of the distal arms 76 as the shape-forming members 74 collapse to a smaller cross-sectional profile. As shown in FIG. 16B, as shape-forming members 74 fully collapse to their smallest cross-sectional profile, distal arms 76 extend at least partially into openings 89. If desired, each shape-forming members 74 can include a lip portion 91 and an intermediate portion 93. Lip portions 91 and intermediate portions 93 can be configured as discussed above with regard to FIGS. 10-13.

The shape-forming members 74 have a non-cylindrical and non-circular cross-sectional profile perpendicular to the main axis of the expander 72, with the main axis being the axis about which the shape-forming members expand. Shape-forming members 74 can be formed of sections that approximate the outer shape of the conduit or orifice into which the frame member or other expandable member is to be position (e.g., the aortic annulus). The plurality of shape-forming members can be formed, as discussed above, with any number of different sections or members. FIG. 15 shows an expander with three shape-forming members; however, there could be as few as two members or there can be more than three members. In addition, as with the expanders discussed above, the collapsed profile of expander 72 is smaller than its expanded profile, permitting expander 72 to more easily enter and exit the body orifice or conduit before and after expansion of the frame member or other expandable member.

Figure 17:
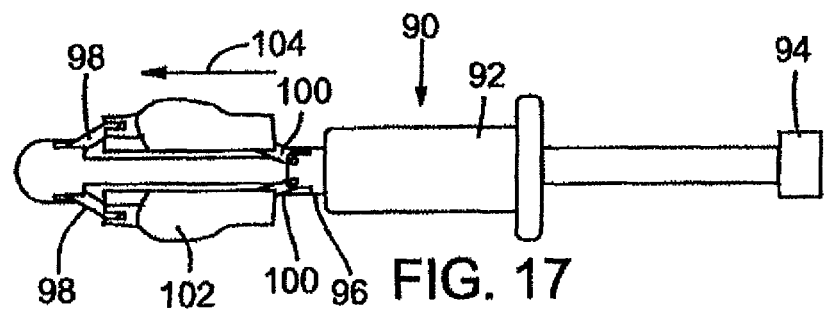
FIG. 17 is a side view of an expanding device.

FIG. 17 shows another embodiment of a mechanical expander. Expander 90 has a moveable handle portion 92 and a shaft portion 94. Shaft portion 94 extends through handle portion 92 and distal arms 98 are pivotably connected to a distal end of shaft portion 94. Proximal arms 100 are pivotably connected to a distal end 96 of handle portion 94. Distal arms 98 and proximal arms 100 are pivotably coupled to shape-forming members 102. By moving handle portion 92 relative to shaft portion 94, shape-forming members 102 can be moved from a first configuration (e.g., an unexpanded configuration) to a second configuration (e.g., an expanded configuration) and vice versa. For example, by holding shaft portion 94 in a fixed position and moving handle portion 92 longitudinally in the direction of the arrow 104, the distal end 96 of handle portion 92 causes proximal arms 100 to move radially outward to expand a prosthetic device (not shown) mounted on the shape-forming members. The outward movement of proximal arms 100 forces shape-forming members 102 to move radially outward. Because distal arms 98 are pivotably coupled to shaft portion 94, the movement of proximal arms 100 radially outward also forces distal arms 98 to move radially outwards.

To collapse the expander 90 and return shape-forming members 102 to an unexpanded configuration, handle portion 92 can be moved longitudinally in the direction opposite arrow 104. By moving handle portion 92 proximally, proximal arms 100 are moved radially inward, which causes shape-forming members 102 to return to an unexpanded configuration.

When the handle portion 92 is moved to a position of maximum expansion, both the proximal and distal arms can extend radially at about 90 degrees from the axis of the shaft portion 94. In its expanded configuration, the expander 90 has a larger diameter than it does in its non-expanded (or collapsed) configuration.

Figure 18A:
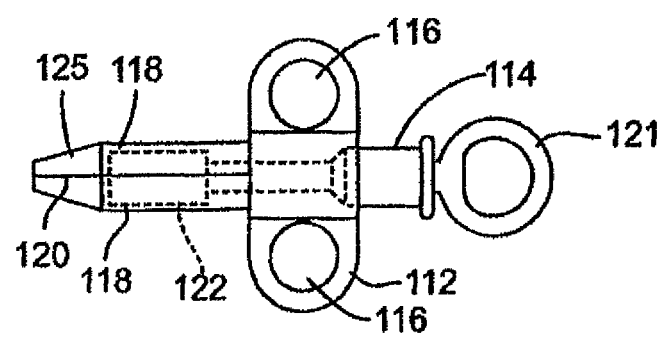
FIG. 18A is a side view of another expanding device, shown in an unexpanded configuration.
Figure 18B:
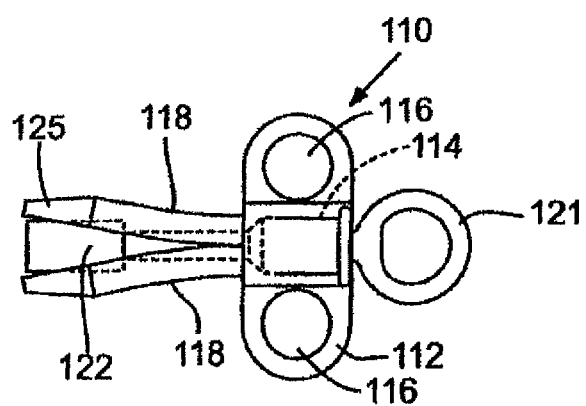
FIG. 18B is a side view of the expanding device of FIG. 18A, shown in an expanded configuration.

FIGS. 18A and 18B show another embodiment of a mechanical expander. An expander 110 includes a handle portion 112 and a plunger portion, or shaft, 114. The handle portion 112 can have one or more finger holes 116 that allow a user to hold handle portion 112 comfortably. The distal end of handle portion 112 has a plurality of flexible finger portions 118, which are connected to the handle portion 112 but separated from one another via one or more slits 120. Handle portion 112 is configured with a passageway or bore extending longitudinally through handle portion 112. Plunger portion 114 is configured to be moveable longitudinally through the bore between a first position (FIG. 18A) and a second position (FIG. 18B). By moving the plunger portion from the first position (FIG. 18A) to the second position (FIG. 18B), the plunger portion 114 can cause finger portions 118 to move radially outward.

Finger portions 118 function as shape-forming members so that radial expansion of finger portions 118 is effective to expand a frame member or other expandable member that is disposed on a distal end 125 of the finger portions 118. Desirably, the distal end portion 125 of the finger portions 118 is tapered to a smaller diameter. In operation, plunger portion 114 (including an enlarged cylindrical portion 122 at the distal end of the plunger) can be moved distally through the handle portion 112 from the first position to the second position. As the cylindrical portion 122 extends into the tapered section of the finger portions 118, the larger diameter of the cylindrical portion 122 forces the tapered section of the finger portions 118 to move radially outward. The radial expansion of the finger portions 118 operates to force the expansion of a frame member that is disposed (or positioned) on the distal end of the finger portions 118.

After the frame member is expanded by the movement of the plunger portion 114 into the opening of handle portion 112, the expander 110 can be collapsed by moving the plunger portion 114 longitudinally in the proximal direction. As the plunger portion 114 moves out of the tapered section of the handle portion 112, the finger portions 118 move radially inward under their own resiliency and the expander can return to its collapsed or unexpanded configuration.

The outer surface of the finger portions 118 that mount the prosthetic device can be configured to conform to an anatomical shape of an orifice or conduit of the body. For example, as shown in FIG. 18B, in its expanded configuration, the finger portions 118 of the handle portion 112 have a smaller diameter at a location nearer the distal end of the finger portions 118 and have a larger diameter at the portion just proximal to the tapered portion. In this manner, finger portions 118 form a non-circular outer envelope curve as discussed above with regard to other embodiments.

Figure 19A:
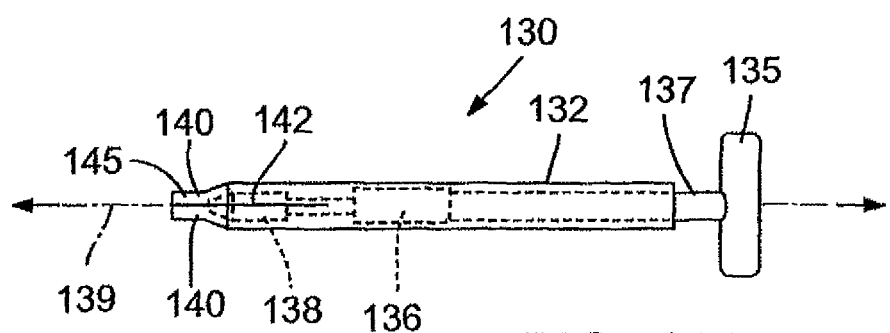
FIG. 19A is a side view of another expanding device, shown in an unexpanded configuration.
Figure 19B:
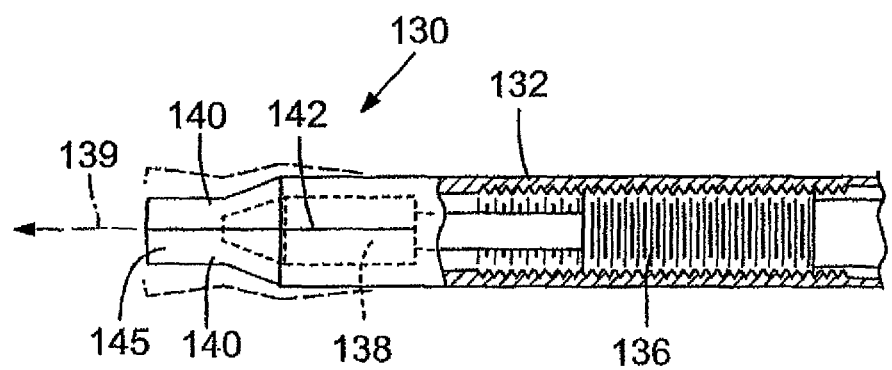
FIG. 19B is a side view of the expanding device of FIG. 18A, shown in an expanded configuration.

FIGS. 19A and 19B illustrate another plunger-type mechanical expander. Expander 130 has a handle portion 132 and a plunger portion 135. The general operation of expander 130 is similar to the expander shown in FIGS. 18A and 18B, except that the relative positions of the handle portion 132 and the plunger portion 135 are changed by rotating the two portions relative to each other.

As in the embodiment described with reference to FIGS. 18A and 18B, plunger portion 135 has an elongated shaft 137 that extends through an opening in handle portion 132. However, unlike FIGS. 18A and 18B, handle portion 132 has an internally threaded portion 133 and shaft 137 has an externally threaded portion 136. Internally threaded portion 133 of handle portion 132 mates with the externally threaded portion 136 of shaft 137 and, when plunger portion 135 is rotated about the main axis 139 of the expander, plunger portion 135 moves longitudinally relative to handle portion 132. By rotating the plunger portion 135, for example, in a clockwise direction (about the axis of the handle and plunger portions) the plunger portion 135 moves further into the opening of handle portion 132 in the distal direction. By rotating the plunger portion 135 in a counter-clockwise direction (about the axis of the handle and plunger portions) the plunger portion 135 moves out of the opening of handle portion 132 in the proximal direction.

As in the embodiment shown in FIGS. 18A and 18B, the distal end portion 145 of the handle portion 132 has flexible finger portions 140 that are separated by slits 142. A radially expandable frame member or other expandable member can be positioned on a tapered (or narrowed) outer surface of distal end portion 145 of handle portion 132 in a crimped or collapsed state. When plunger portion 135 is rotated clockwise, an enlarged cylindrical portion 138 of the shaft 137 extends further into the opening of the handle portion 132 and eventually moves into the tapered portion of handle portion 132. Once the enlarged cylindrical portion 138 extends into the tapered portion of the finger portions 140, the finger portions 140 are forced radially outward. The force of the radial expansion of the finger portions 140 causes the expansion of the frame member positioned on the distal end portion 145 of the handle portion 132.

Figures 20A, 20B:
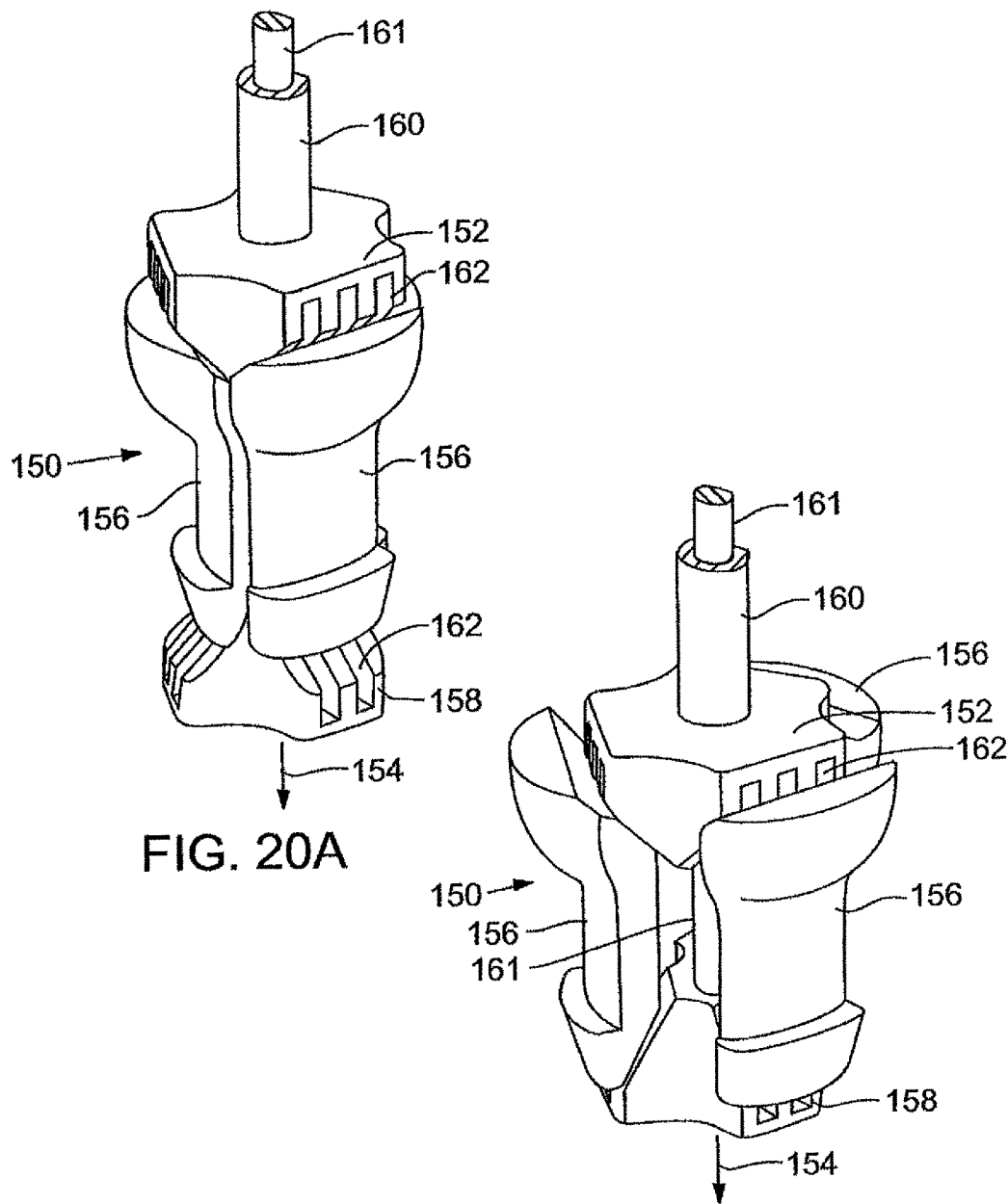
FIG. 20A is a perspective view of an expanding device, shown in an unexpanded configuration.
FIG. 20B is a perspective view of the expanding device of FIG. 20B, shown in an unexpanded configuration.

FIGS. 20A and 20B show another embodiment of a mechanical expander in a collapsed state (FIG. 20A) and an expanded state (FIG. 20B). As shown in FIG. 20A, expander 150 can include a wedge member 152 that can move longitudinally along axis 154. A plurality of shape-forming members 156 can be slidably connected to wedge member 152 and configured such that longitudinal movement of wedge member 152 forces the shape-forming members radially outwards or radially inward, depending on the direction of movement of wedge member 152.

Shape-forming members 156 can also be connected to a cap member 158 at the distal end of the expander. Wedge member 152 is fixedly connected to the distal end of a main shaft 160 and can be moved longitudinally along axis 154 by moving shaft 160. Shaft 160 desirably has a handle portion (not shown) at the proximal end of shaft 160 to facilitate movement of shaft 160 relative to an inner shaft 161. Inner shaft 161 extends through main shaft 160 and is connected at its distal end to cap member 158. Main shaft 160 is moveable longitudinally relative to the inner shaft 161 to move wedge member 152 relative to shape-forming members 156 and cap member 158. Wedge member 152 and/or cap member 158 can have slots 162 formed in an outer surface thereof. Shape-forming members 156 can be mounted to wedge member 152 and/or cap member 158 via projections formed on the inner surfaces of the shape-forming members and which extend into slots 162.

The projections can extend from shape-forming members 156 into slots 162, thereby securing shape-forming members 156 to the wedge member 152 and/or cap member 158. The projections desirably are configured to permit shape-forming members 156 to move relative to the wedge member 152 and the cap member 158, but prevent shape-forming members 156 from separating from wedge member 152 and/or cap member 158. In operation, as shaft 160 is moved distally (in the direction of axis arrow 154), wedge member 152 slides distally, moving shape-forming members 156 radially outward from the collapsed state (FIG. 20A) to the expanded state (FIG. 20B). At the same time shape-forming members 156 move distally along the outer surface of cap member 158.

Figure 21:
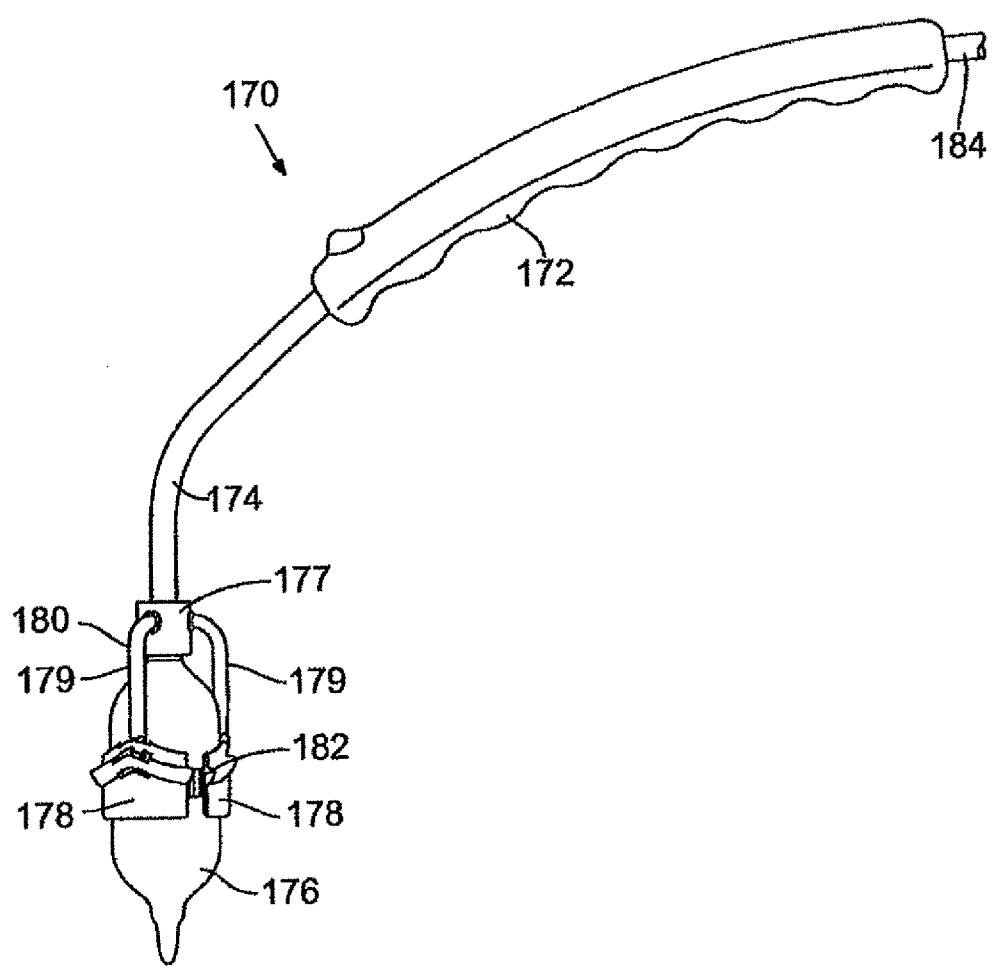
FIG. 21 is a side view of an expanding device, shown in an expanded configuration.

FIG. 21 shows another embodiment of an expander. Expander 170 is a hybrid of a balloon expander and a mechanical expander. As in the embodiment shown in FIG. 4, expander 170 includes a handle 172, a shaft 174, and an expandable balloon member 176. In addition, shape-forming members 178 surround balloon member 176 as part of an external frame 180 that is not directly attached to balloon member 176. The external frame comprises a proximal portion 177 (proximal to the balloon member 176) mounted on the distal end portion of shaft 174, elongated arms 179 that extend from the proximal portion 177, and shape-forming members 178 that are coupled to the distal ends of arms 179 and which at least partially surround the balloon member 176. Any number of arms can be used to secure the shape-forming members to the proximal portion 177 of the external frame 180; however, desirably, there are at least two arms and desirably, the number of arms corresponds to the number of shape-forming members 178.

As in the embodiment of FIG. 4, shaft 174 desirably comprises a lumen that extends from the proximal end of the handle 184 to the proximal end of balloon member 176. The lumen of shaft 174 is in fluid communication with balloon member 176. An inflating device (not shown) can be connected to the proximal end 184 of the shaft 174 and a fluid that is capable of inflating the balloon member 176 can be transferred from the inflating device through the fluid passageway to balloon member 176 via the lumen of shaft 174. Balloon inflating devices are well known and any conventional inflation means can serve to inflate balloon member 176 to expand the shape-forming members 178.

In addition to having an external frame 180, the expander 170 can include one or more locking members 182 that connect the shape-forming members 178 to one another. The locking member 182 at least partially surrounds balloon 176 and can have a structure that permits the shape-forming members to expand radially away from one another, but restricts movement of the shape-forming back towards an unexpanded configuration.

As seen in FIG. 21, locking members 182 can have grooves that lock (or hold) the expander 170 in any of a plurality of expanded positions. In particular, the grooves (or teeth) can mate with opposing grooves (or teeth) on the inside of shape-forming members 178, permitting the shape-forming members 178 to move away from one another, while at the same time preventing them from collapsing back towards each other after the balloon member 176 is deflated. As the balloon member 176 inflates, the radial force from the expanding balloon member 176 forces the shape-forming members 178 to move radially outward and the locking members 182 hold the shape-forming members 178 in the expanded position. If desired, a release mechanism can be provided. For example, a wire can be provided that releases the locking members from their locked position (e.g., by pulling the grooves or teeth radially inward). The wire (or release mechanism) can extend from the locking member through the arms and up the shaft 174, and can be accessible at the handle 172.

Figure 22:
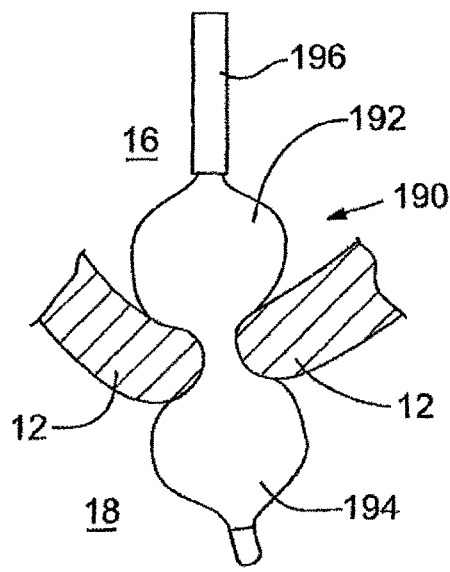
FIG. 22 is a partial cross section view of an expanding device positioned at an orifice of a heart and shown in an expanded configuration.

For example, as shown in FIG. 22, a balloon member 190 can be configured with a center longitudinal portion and a first portion 192 that extends into the aorta 16 and a second portion 194 that extends into the left ventricle 18. The first and second portions 192, 194 can have a larger diameter than the center portion. Second portion 194 of balloon member 190 can be introduced into the left ventricle 18 in a collapsed (non-expanded) state so that second portion 194 can easily pass through the annulus 12. Once properly position within the annulus 12, balloon member 190 can be inflated (expanded) in the manner discussed above with regard to other embodiments. In operation, a frame or other expandable member can be crimped on balloon member 190 (or otherwise positioned at the treatment site for expansion). Balloon member 190 can have shape-forming members (not shown in FIG. 22, but as described in detail herein) positioned on the balloon member 190 beneath the location of the crimped, mounted valve.

Desirably, the frame member can be positioned so that it will contact both first and second portions of balloon member 190 during expansion. After positioning (or mounting) the frame member on the balloon member 190 and then positioning the frame member and balloon member at the deployment location, the balloon member 190 can be inflated as described above and the frame member can be expanded to the desired shape.

The inflation of balloon member 190 can be achieved in a single stage or in multiple stages. A single stage inflation can be achieved by having a single lumen that inflates both first portion 192 and second portion 194. Once the balloon member 190 is in position, fluid can pass through a lumen in a balloon catheter 196 (or other shaft that has a lumen that is in fluid connection with the balloon member and the fluid pressurizing device) to the balloon member 190, thereby inflating first portion 192 and second portion 194 substantially simultaneously.

Alternatively, the inflation of balloon member 190 can be achieved in two stages. Separate lumens (not shown) can be connected to first portion 192 and second portion 194 to allow for the inflation of first portion 192 and second portion 194 to be separately achieved. Expanding the portion of the balloon member 190 that is in the ventricle area first can provide better visibility for proper anatomical placement of the second portion 194 of balloon member 190. That is, it may be desirable to inflate second portion 194 on the left ventricle 18 side of the annulus 12 prior to inflating first portion 192. After second portion 194 is inflated, first portion 192 can be inflated on the aorta 16 side of the annulus 12.

Figure 23A:
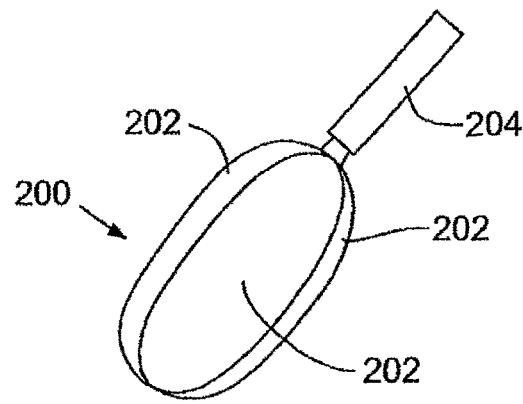
FIG. 23A is a side view of an expanding device, shown in an expanded configuration.
Figure 23B:
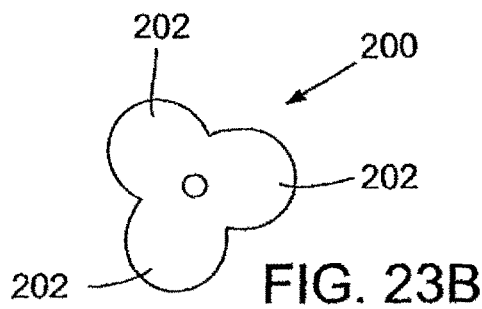
FIG. 23B is a bottom view of the expanding device of FIG. 23A.

FIGS. 23A and 23B show another embodiment in which an expanding member is constructed so that it can expand a frame member or other expandable member to conform to a particular anatomical shape having a non-circular cross-sectional profile. In this embodiment, a balloon member 200 is constructed with three lobes 202 that are shaped to conform to the aortic root at the aortic valve annulus, as shown in FIGS. 2 and 3 above. Balloon member 200 can expand a frame member (such as frame member 70 shown in FIGS. 14A and 14B) to have a trilobular shape to conform to the natural anatomical configuration of the aortic root at the aortic valve annulus.

Balloon member 200 can be formed with three distinct chambers that each form one of the three lobes 202. Each of the three lobes 202 can be pressurized via a lumen in a balloon catheter shaft 204 (or other shaft that has a lumen that is in fluid connection with the balloon member and the fluid pressurizing device). Three separate lumens can be connected to each of lobes 202. Desirably, however, a single lumen is connected to the three lobes. In this manner, each lobe 202 is connected to the same fluid supply, which permits quick and uniform expansion of the three lobes 202. When balloon member 200 is fully inflated, the lobes 202 collectively form a trilobular cross-sectional profile (as best shown in FIG. 23B) that generally conforms to the anatomical shape of the aortic root at the valve annulus.

Balloon member 200 can be formed with lobes 202 by molding the balloon member 200 so that it has the desired shape. Alternatively, three separate balloon members can be heat sealed together to form the trilobular shape of balloon member 200. The three separate balloon members can be connected to the same fluid source at a proximal end of the balloon member 200 in a manner that is similar to the construction of air coils on a floatation raft for a swimming pool.

The embodiment of FIG. 22 can be combined with the embodiment shown in FIGS. 23A and 23B to form a balloon member with four sections. Such a balloon member can have the three section trilobular configuration (as shown in FIG. 23A) forming first portion 192 (as described above with regard to FIG. 22) and the second portion 194 being formed as shown in FIG. 22. With such a construction, second portion 194 can expand the portion of a frame member that is in left ventricle and the trilobular configuration of first portion 192 can expand the portion of a frame member that is in the aorta. The portion of frame member that is expanded by the trilobular configuration of first portion 192 is expanded to have a similar trilobular shape that generally conforms to the trilobular shape of the aortic root.

Figure 24A:
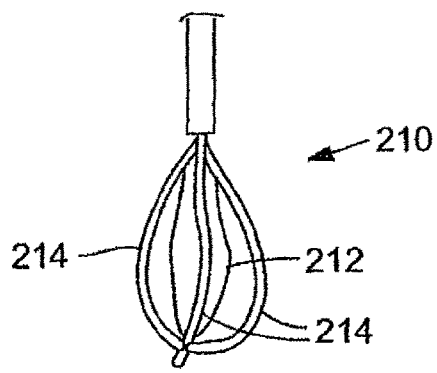
FIG. 24A is a side view of an expanding device, shown in an unexpanded configuration.
Figure 24B:
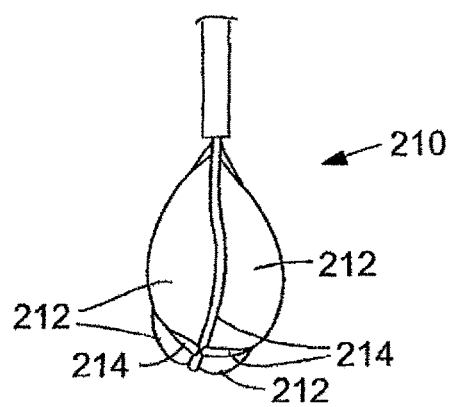
FIG. 24B is a bottom view of the expanding device of FIG. 24A, shown in an expanded configuration.

FIGS. 24A and 24B show another embodiment in which a balloon member is constructed so that it can expand a frame member or other expandable member to conform to a particular anatomical shape having a non-circular cross-sectional profile. In this embodiment, a balloon member 210 includes a balloon member 212 and a shape-forming member (balloon-restricting member) 214. Shape-forming member 214 comprises wire members that restrain the expansion of balloon member 212 and cause the balloon member to assume a desired non-circular cross section when expanded. The shape-forming member 214 can be formed in a variety of configurations. FIG. 24A shows a shape-forming member comprising three wires 214 positioned about the balloon member such that the balloon member, when expanded, is restrained where the balloon member contacts each wire 214. By restraining the expansion of balloon member 212 in this manner, the balloon member 210 will form a trilobular shape when the balloon member 212 is fully expanded.

FIG. 24A shows balloon member 212 in a deflated state inside of shape-forming member 214. When balloon member 212 is expanded inside shape-forming member 214, the three wire members of shape-forming member 204 restrict the expansion of the balloon member 212 at the location of the wire members, but permit the expansion of the balloon member 212 in the areas between the wire members. Accordingly, as shown in FIG. 24B, the balloon member 212 expands into a trilobular configuration. Consequently, balloon member 210 can expand a frame member (such as frame member 70 shown in FIGS. 14A and 14B) to have a trilobular shape that generally conforms to the natural anatomical configuration of the aortic root at the aortic valve annulus.

FIGS. 25A, 25B, 26A, and 26B show another embodiment in which a balloon member is constructed so that it can expand a frame member or other expandable member to conform to a particular anatomical shape. In this embodiment, a balloon member 220 includes a balloon member 224 and a shape-forming member (balloon-restricting member) 226. Shape-forming member 226 can be a relatively rigid member (at least compared to balloon member 224) that has one or more openings 222. The embodiment shown in FIG. 26A has three openings spaced approximately 120 degrees apart (as measured from the center of each opening). By constructing shape-forming member 226 with three openings in this manner, when balloon member 224 is inflated within shape-forming member 226, balloon member 224 extends out of shape-forming member 226 at the locations of the openings. As shown in FIG. 26A, after inflation of balloon member 224, the resulting shape of balloon member 220 at the balloon member is trilobular.

FIG. 25A shows balloon member 224 in a deflated state inside of shape-forming member 226. When balloon member 224 is expanded inside shape-forming member 226, shape-forming member 226 restricts the expansion of balloon member 224 except at the locations of the openings. Accordingly, as shown in FIGS. 26A and 26B, balloon member 224 expands into a trilobular configuration. Consequently, balloon member 220 can expand a frame member (such as frame member 70 shown in FIGS. 14A and 14B) to have a trilobular shape that generally conforms to the natural anatomical configuration of the aortic root at the aortic valve annulus.

In addition, it should be noted that although the embodiments discussed above depict methods for expanding frames or other expandable members using surgical methods to access an orifice or conduit of the body, such expanders could also be used in procedures where access to the orifice or conduit is achieved through the patient's vasculature in a percutaneous delivery approach (e.g., via a femoral artery). For example, as shown in FIG. 6, a balloon member 32 with shape-forming members 34 can be collapsed down to a smaller diameter. The ability to collapse the balloon member 32 and shape-forming members 34 to a smaller diameter enables the device to be passed through a patient's vasculature to arrive at a treatment site. Accordingly, the expanders described above could be combined with a conventional balloon catheter that is sized to be passed through the vasculature of a patient (using a separate guide catheter if desired) to reach an orifice or conduit in the body in which it is desired to expand a frame member or other expandable member.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An apparatus for radially expanding a prosthetic device in a conduit or orifice of a human body, the apparatus comprising:

a delivery shaft having a lumen therethrough;

a prosthetic device comprising a frame member; and a balloon member mounted on a distal end of the delivery shaft, the balloon member having a main axis and an outer mounting surface for mounting the prosthetic device in a crimped state thereon, the balloon member being configured to expand from a non-expanded state to an expanded state when pressurized by fluid passed through the lumen of the delivery shaft; and a balloon-restricting member surrounding at least a portion of the balloon member and forming a portion of the outer mounting surface, the balloon-restricting member having a plurality of openings through which portions of the balloon member extend when the balloon is in the expanded state, wherein the plurality of openings are configured so that when the balloon member is in the expanded state, the balloon member has an outer profile that is non-circular in cross section perpendicular to the main axis of the balloon member; and wherein the balloon member is configured to expand radially outwards from the non-expanded state to the expanded state to expand the prosthetic device to an expanded shape having a non-circular cross-sectional profile perpendicular to the main axis of the balloon member.

2. The apparatus of claim 1, wherein the prosthetic device is a prosthetic heart valve.

3. The apparatus of claim 1, wherein the balloon-restricting member comprises a wire frame.

4. The apparatus of claim 1, wherein the balloon-restricting member comprises a tube, the tube defining the plurality of openings.

5. The apparatus of claim 1, wherein the balloon member is configured to expand the prosthetic device to generally conform to an anatomical shape of the conduit or orifice.

6. The apparatus of claim 1, wherein the balloon member in its expanded state has a distal portion and a proximal portion separated by a center longitudinal portion, and wherein the distal and proximal portions both have a larger diameter than the center portion.

7. The apparatus of claim 1, wherein the non-circular cross-sectional profile is a three-lobed shape in radial cross-section.

8. The apparatus of claim 7, wherein the balloon member in its expanded state has a distal portion and a proximal portion separated by a center longitudinal portion, and wherein the distal and proximal portions both have a larger diameter than the center portion.

9. The apparatus of claim 1, wherein the balloon member in its expanded state has three lobes distributed circumferentially that are shaped to conform to the aortic root at the aortic valve annulus.

10. The apparatus of claim 9, wherein the balloon member is formed with three distinct chambers that each form one of the three lobes, and the three chambers are simultaneously pressurized by fluid passed through the lumen of the delivery shaft.

11. The apparatus of claim 9, wherein the balloon member is formed with three distinct chambers that each form one of the three lobes, and the three chambers are individually pressurized.

12. The apparatus of claim 9, wherein the balloon member has four chambers including the three distinct chambers in a proximal portion and a distal portion with just one chamber.

13. An apparatus for radially expanding a prosthetic device in a conduit or orifice of a human body, the apparatus comprising:

a delivery shaft having a lumen therethrough;

a balloon member mounted on a distal end of the delivery shaft, the balloon member having a main axis and an outer mounting surface for mounting the prosthetic device in a crimped state thereon, the balloon member being configured to expand from a non-expanded state to an expanded state when pressurized by fluid passed through the lumen of the delivery shaft, and a balloon-restricting member surrounding at least a portion of the balloon member, the balloon-restricting member having a plurality of openings through which portions of the balloon member extend when the balloon member is in the expanded state to expand the prosthetic device crimped thereon, wherein the plurality of openings are configured so that when the balloon member is in the expanded state, the balloon member has an outer profile that is non-circular in cross section perpendicular to the main axis of the balloon member so that the prosthetic device has an expanded shape having a non-circular cross-sectional profile perpendicular to the main axis of the balloon member.

14. The apparatus of claim 13, wherein the balloon-restricting member comprises a wire frame.

15. The apparatus of claim 14, wherein the wire frame comprises three wires that extend from a distal end of the shaft around the balloon member and join at a central point distal to the balloon member.

16. The apparatus of claim 13, wherein the balloon member in its expanded state has three lobes distributed circumferentially that are shaped to conform to the aortic root at the aortic valve annulus.

17. The apparatus of claim 13, wherein the balloon member is configured to expand the prosthetic device to generally conform to an anatomical shape of the conduit or orifice.

18. The apparatus of claim 13, wherein the balloon member in its expanded state has a distal portion and a proximal portion separated by a center longitudinal portion, and wherein the distal and proximal portions both have a larger diameter than the center portion.

19. The apparatus of claim 13, wherein the balloon-restricting member comprises a tube, the tube defining the plurality of openings.

20. The apparatus of claim 19, wherein the balloon-restricting member has three openings spaced approximately 120 degrees apart so as to expand the balloon member in a three-lobed shape.

21. The apparatus of claim 13, wherein the non-circular cross-sectional profile is a three-lobed shape in radial cross-section.

22. The apparatus of claim 21, wherein the balloon member is formed with three distinct chambers that each form one of the three lobes, and the three chambers are simultaneously pressurized by fluid passed through the lumen of the delivery shaft.

23. The apparatus of claim 21, wherein the balloon member is formed with three distinct chambers that each form one of the three lobes, and the three chambers are individually pressurized.

24. The apparatus of claim 21, wherein the balloon member has four chambers including the three distinct chambers in a proximal portion and a distal portion with just one chamber.

* * * * *